(12) United States Patent
Isami

(10) Patent No.: US 7,085,669 B2
(45) Date of Patent: Aug. 1, 2006

(54) METHOD AND SYSTEM OF PRODUCING ANALYTICAL DATA RESULT

(75) Inventor: Yasushi Isami, Himeji (JP)

(73) Assignee: Sysmex Corporation, Kobe (JP)

( * ) Notice: Subject to any disclaimer, the term of this patent is extended or adjusted under 35 U.S.C. 154(b) by 646 days.

(21) Appl. No.: 09/934,521

(22) Filed: Aug. 23, 2001

(65) Prior Publication Data

US 2002/0026292 A1 Feb. 28, 2002

(30) Foreign Application Priority Data

Aug. 25, 2000 (JP) ............................. 2000-255338
Aug. 3, 2001 (JP) ............................. 2001-236296

(51) Int. Cl.
*G06F 15/00* (2006.01)

(52) U.S. Cl. ...................... 702/127; 702/122

(58) Field of Classification Search ................ 702/19, 702/21–23, 25, 27, 30–32, 122, 183, 188, 702/127; 600/300, 310, 368; 705/2; 713/200
See application file for complete search history.

(56) References Cited

U.S. PATENT DOCUMENTS

| | | | | |
|---|---|---|---|---|
| 4,491,725 A | * | 1/1985 | Pritchard | 705/2 |
| 4,998,533 A | * | 3/1991 | Winkelman | 600/368 |
| 5,630,413 A | * | 5/1997 | Thomas et al. | 600/310 |
| 5,781,723 A | * | 7/1998 | Yee et al. | 713/200 |
| 6,059,692 A | * | 5/2000 | Hickman | 482/8 |
| 6,135,949 A | * | 10/2000 | Russo et al. | 600/300 |
| 6,306,087 B1 | * | 10/2001 | Barnhill et al. | 600/300 |
| 6,331,822 B1 | * | 12/2001 | Sato et al. | 340/3.22 |
| 6,368,795 B1 | * | 4/2002 | Hefti | 435/6 |
| 6,398,727 B1 | * | 6/2002 | Bui et al. | 600/300 |
| 6,581,012 B1 | * | 6/2003 | Aryev et al. | 702/22 |
| 6,602,191 B1 | * | 8/2003 | Quy | 600/300 |
| 6,616,613 B1 | * | 9/2003 | Goodman | 600/504 |
| 6,709,399 B1 | * | 3/2004 | Shen et al. | 600/508 |

OTHER PUBLICATIONS

James Heller, William McMahan, Nancy Bryan, an in-vivo test system for electrochemical sensors, 1988, Medical Instrument Systems Research Division.*

J. E. Chomas, R. A. Sikes, K. W. Ferrara, correlation analysis of received echoes from contrast agents in-vitro and in-vivo, 199 University of virginia, Department of Biomedical Engineering, University of Virginia, department of Oncology.*

* cited by examiner

*Primary Examiner*—Marc S. Hoff
*Assistant Examiner*—Mohamed Charioui
(74) *Attorney, Agent, or Firm*—Global IP Counselors, LLP

(57) ABSTRACT

An object of the present invention is to reduce the burden of purchasing measurement devices for clinical tests, and to simplify user support for the measurement devices. Divide the measurement function of a clinical test device and the analysis function between the medical institution and a service provider. In other words, the measurement of clinical data occurs in a measurement device 2 of a medical institution, and the analysis of the measurement data occurs in an analysis server 1. Due to this, measurement data is transmitted via a network 3 from measurement device 2 to analysis server 1. In addition, analytical data is transmitted via network 3 from analysis server 1 to an output terminal 4. The service provider provides measurement device 2 to the medical institution free of charge, and in return collects a use fee from the medical institution for the analysis service.

36 Claims, 17 Drawing Sheets

Conceptual view of a user DB

| User ID | U—sysmex |
|---|---|
| User Name | Sysmex Hospital |
| Contact Person | Test Dept.: Tanaka |
| Contract details | 123-4567 |
| Service usage<br>    BASIC<br>    C001<br>    C002 | <br>100<br>60<br>37 |

*Fig. 4*

Conceptual view of contact DB

| Contract details | Analysis service | Test Items | Basic contract flag | Basic fee | Maximum |
|---|---|---|---|---|---|
| 123-4567 | C001 | APTT, PT, Fbg | Yes | ¥15,000 | 100 |
| 123-4567 | C001 | APTT, PT, Fbg | Yes | ¥200 | |
| 123-4567 | C002 | TTO | No | ¥450 | |

Fig. 5

| | |
|---|---|
| User ID | U-sysmex |
| Specimen ID | 01-001 |
| Device ID | M103 |
| Parsing order | 6789 |
| Sample classification | Blood |
| Test item | PT |
| Measurement item | PT |
| Device type | Sysmex CA-1500 |
| Device version | Ver. 03 |
| Reply address | out@U-sysmex. co. jp |
| Correction value | 1 |
| Measurement data | (2 sec. 28), (2.1 sec. 31), (2.2 sec. 35) |

*Fig. 6*

Working data transmitted to output terminal from analysis server

| User ID | U—sysmex |
|---|---|
| Specimen ID | 01-001 |
| Device ID | M103 |
| Parsing order | 6789 |
| Sample classification | Blood |
| Test item | PT |
| Device version | Sysmex CA-1500 |
| Analytical data | 11.0 sec. |
| Supplemental Information | 110.5% 1.04 1.07INR |

Flow of analysis process

METHOD AND SYSTEM OF PRODUCING ANALYTICAL DATA RESULT

BACKGROUND OF THE INVENTION

1. Technical Field

The present invention relates to technology for obtaining analytical data by means of clinical tests and for delivering that data to a medical institution.

In the present invention, measuring devices take measurements for in vivo tests, in vitro tests, and the like, and have a feature that outputs measurement data. In addition, an analysis device analyzes the aforementioned measurement data obtained by the measurement devices, and has a feature that outputs analytical data. A testing device combines both features of the aforementioned measurement devices and the aforementioned analysis device.

2. Description of Related Art

In medical institutions such as hospitals and the like, clinical tests are performed to diagnose such things as the physical condition of patients and the diseases that afflict them. These clinical tests are roughly classified as in vitro tests on samples of blood, urine, and the like collected from a patient as a subject, and in vivo tests that are performed directly on the subject, such as an electrocardiogram, an ultrasound examination, and the like. Testing devices that employ these tests normally include a measurement unit that measures samples collected from a subject, biological changes, and the like, and an analysis section that analyzes the measurement data obtained from the aforementioned measurements. In addition, the testing device is furnished with a display section, a sample processing section, and the like as needed. The performance of this type of testing device depends not only on the measurement principle, the structural layout, and the like, but also on programs that do such things as control and monitor the operation of the testing device, analyze measurement data, and the like. Thus, it is often the case that even with the same testing device, different programs are loaded onto the device in order to achieve the functions needed by the medical institution. These programs are generally upgraded to their most recent version.

Medical institutions obtain testing devices and use these to perform clinical tests. However, there are times when test items must change depending on changes in the medical environment, and one must see to it that these new test items can be tested. In addition, there are also times when exceedingly accurate test methods on the same test items are established, and one must see to it that these new test methods can be implemented. However, even in these types of situations, there are situations that can be dealt with by changing the program that analyzes the measurement data, and situations in which replacing the entire testing device is not necessary.

However, the programs that analyze measurement data in a conventional testing device are installed on the inside thereof. In order to change a program, a version upgrade of the program must be requested to the company that provides support service for the testing device (hereinafter, "support service provider"), or a copy of the program must be obtained and the user of the testing device (hereinafter, "user") must install it. With this, it is difficult for the user to flexibly deal with changes to the medical environment.

Moreover, the user must acquire a testing device in order to conduct clinical tests, but it is normally quite expensive. Because of that, the user needs at least 2 to 3 years to recover the cost of acquiring the device by means of testing fees. Thus, the user is forced into a large initial investment in order to conduct clinical tests, and must shoulder an economically large burden.

On the other hand, the problems to be solved by the present invention will be considered from the standpoint of the support service provider.

It is common that testing devices are equipped with various program versions for a variety of testing needs. There is a problem that support service providers find it difficult to provide a detailed level of user support unless they manage not only the number of types of testing devices that users have, but also the versions of the programs running in each testing device. For example, in the event they determine that a certain version of a program is not operating properly, it is difficult to deal smoothly with this situation if the testing device in which the program is loaded cannot be identified. For example, in the event they determine that a certain version of a program is not operating properly, it is difficult to deal smoothly with this situation if the testing device in which the program is loaded cannot be identified.

SUMMARY OF THE INVENTION

An object of the present invention is to allow the user to quickly deal with changes in the medical environment.

It is a further object of the present invention to allow a service support provider to provide a detailed level of user support.

It is a further object of the present invention to reduce the burden of the user's initial investment.

In order to solve the aforementioned problems, a first aspect of the present invention provides a method of providing analytical data that includes the following steps:

a measurement step of calculating measurement data by means of a measurement device for a subject's in vivo test and/or in vitro test, a first transmission step of transmitting the measurement data from the measurement device to an analysis device via a network, a first receiving step of receiving the measurement data by the analysis device, an analysis step of analyzing the measurement data by the analysis device to obtain analytical data, a second transmission step of transmitting the analytical data from the analysis device, via the network, to the measurement device, and a second receiving step of receiving the analytical data by the measurement device.

Here, the measurement data obtained by the measurement device is preliminary information, and the user cannot report this data as test results. The analysis device has a feature that converts the form of the measurement data that the user can report as test data to the subject. The test results are referred to as analytical data.

A system adopting this method will be described by using the measurement and analysis of blood as an example. A measurement device that measures blood and an output device that outputs analytical data are installed by a user such as a medical institution and the like. The measurement device and output device may be substantially effectuated by using one computer, and may be effectuated by using separate computers. On the other hand, the analysis device is effectuated by a computer in which a program for analyzing blood measurement data sent from a measurement device is installed. This computer is installed in a service provider that provides analytical data. The analysis device, measurement device, and output device are connected by a network, such as a public telephone network, a mobile communications network, an ISDN, or the like. In a system constructed in this manner, only the output of blood measurement and analytical data occurs on the user's side, and only the analysis of measurement data occurs on the service provider's side. In addition, the measurement objects are not limited to samples. For example, an electrocardiogram or an electric scan of a patient's stomach can be sent to the analysis device as a subject's measurement data, and the analysis data can be returned from the analysis device.

By employing the method of the present aspect, even if a user needed an analysis program corresponding to a new test method, the service provider may only upgrade the analysis program of the analysis device. Thus, the user can omit the time required for getting a program from the service provider, installing it, and the like, and can quickly respond to changes in the medical environment. On the other hand, the service provider is freed from the burden of having to manage the program categories of the test devices installed in each user, let alone the versions.

A specific example of the measurement device, measurement data, analysis device and analytical data will be described by using the time it takes for blood to coagulate, in other words, a test of blood coagulation time. This test is a test that measures blood coagulation time by receiving blood in a clear container and adding a predetermined reagent. A commonly requested method of measurement and analysis is: a light source and a photoreceptor are disposed on both sides of the clear container that received the blood, the intensity of the light that photoreceptor receives (hereinafter, the degree of light scattering) is measured in time series, and the blood coagulation time is calculated from the degree of light scattering obtained. Thus, the measurement device is composed of and includes a container receiving section for receiving the clear container, a light source, a photoreceptor, and a computer that measures the degree of light scattering in time series. The analysis device that analyzes the measurement data is a computer that calculates the blood coagulation time from the degree of light scattering. The analytical data obtained from the analysis device is the blood coagulation time.

The second aspect of the present invention provides a method of producing analytical data according to the first aspect, wherein the first transmission step includes a step of associating a communication address of the measurement device with the measurement data.

In the previously discussed system, the measurement device communicates the communication address of analytical data reply to the analysis device in the event that there are multiple measurement devices corresponding to one analysis device, and in the event that the communication address of the analysis data reply is not in the analysis data.

The third aspect of the present invention provides a method of producing analytical data that includes the following steps:

a measurement step of calculating measurement data by means of a measurement device for a subject's in vivo test and/or in vitro test, a first transmission step of transmitting the measurement data from the measurement device to an analysis device via a network, a first receiving step of receiving the measurement data by the analysis device, an analysis step of analyzing the measurement data by the analysis device to obtain analytical data, a second transmission step of transmitting the analytical data from the analysis device, via the network, to an output device that outputs the analytical data, a second receiving step of receiving the analytical data by the output device, and an output step of outputting the analytical data by the output device.

This aspect produces the same functional effect as the first aspect.

The fourth aspect of the present invention provides a method of producing analytical data according to the third aspect, wherein the first transmission step includes a step of associating a communication address of the output device with the measurement data.

This aspect produces the same functional effect as the second aspect.

The fifth aspect of the present invention provides an analytical data producing device, comprising:

connection means for connecting, via a network, a measurement device that conducts measurements for a subject's in vivo test and/or in vitro test and calculates measurement data, receiving means for receiving the measurement data from the measurement device via the connection means, analysis device for conducting an analysis of the measurement data, and calculating analytical data, and transmission means for transmitting, via the connection means, the analytical data to the measurement device.

This device corresponds to the analysis device of the first aspect.

The sixth aspect of the present invention provides an analytical data producing device according to the fifth aspect, wherein:

the receiving means receives a communication address of the measurement device and associates the communication address with the measurement data.

This device corresponds to the analysis device of the second aspect.

The seventh aspect of the present invention provides the analytical data producing device according to the fifth aspect, wherein:

the receiving means further receives identification information and test items for the subject that are associated with the measurement data, and the transmission means transmits the identification information of the subject and the test items associated with the measurement data.

For the subject's identification information, a specimen number that is employed by each user can be provided. As for test items, they are each type of clinical test, such as a blood test, a blood coagulation test, an immune test, a physiological test, and the like. A test item may not necessarily be one test. In the event that a plurality of test items are measured simultaneously, a plurality of test items can be sent and received.

The eighth aspect of the present invention provides an analytical data producing device according to the fifth aspect, wherein:

the receiving means further receives device identification information that identifies a class of the measurement device and the measurement data associated therewith, and the analysis means including:

storage means for storing analysis methods of the measurement data for each class of the measurement device, determination means for determining the class of the measurement device based upon the measurement identification information, and selection means for selecting an analysis method corresponding to the class of the measurement device from amongst the stored analysis methods, and for applying the same to analysis of the measurement data.

The class of measurement device identifies the type of measurement device and the version of the measurement program that operates the measurement device. This is because there are times when the program that analyzes the measurement data differs according to the type of measurement device that the user employs and the version. For example, there are cases that can be cited in which one user is equipped with a plurality of types of measurement devices, such as a blood cell counter and a blood coagulation device. As a further example, because one user employs a plurality of one type of measurement device, and the measurement programs and the measurement principle differ according to the device, there are cases that can be cited in which the programs that analyze these measurement data are each different.

The ninth aspect of the present invention provides the analytical data producing device according to the fifth aspect, comprising:

results storage means for storing conditions on a contract relating to analysis of measurement data exchanged between a manager of the analytical data producing device and a manager of the measurement device, and usage results of the analytical data production device that the manager of the measurement device used, and determination means for determining items billed to the manager of the measurement device based on the contract conditions and the usage results.

Here, the manager of the analytical data producing device is the service provider that provides the analytical data. The manager of the measurement device is the user. The service provider provides the measurement devices to the user free of charge, and in exchange the user entered into a contract with the service provider in which a fee is charged in response to the frequency of use of the analytical data production service (hereinafter, simply referred to as "analysis service"). For the user, a large initial investment is not necessary, and it becomes easier to respond to changes in the medical environment.

For example, in cases in which the measurement device is a device that measures the coagulation time of blood, a basic contract for up to 100 specimens provides an analytical data production service of 3 basic coagulation tests (APTT, PT, Fbg) for a monthly fee of 15,000 yen. In the event that the number of specimens exceeded 100, an additional charge of 200 yen would be charged per 1 test as outside the basic contract. In addition, analysis service for test items outside the basic contract, for example TTO, is provided at 450 yen per 1 specimen.

The tenth aspect of the present invention provides an analytical data producing device, further comprising:

connection means for connecting, via a network, a measurement device that conducts measurements for a subject's in vivo test and/or in vitro test and calculates measurement data, receiving means for receiving the measurement data from the measurement device via the connection means, analysis device for conducting an analysis of the measurement data, and calculating analytical data, and transmission means for transmitting, via the connection means, the analytical data to an output device that outputs the analytical data.

This aspect produces the same functional effect as the fifth aspect.

The eleventh aspect in the present invention provides an analytical data producing device according to the tenth aspect, wherein:

the receiving means receives a communication address of the measurement device and associates the communication address with the measurement data.

This aspect produces the same functional effect as the sixth aspect.

The twelfth aspect in the present application provides the analytical data producing device according to the tenth aspect that further has the following requirements:

the receiving means further receives identification information and test items for the subject that are associated with the measurement data, and the transmission means transmits the identification information of the subject and the test items associated with the analytical data.

This aspect produces the same functional effect as the seventh aspect.

The thirteenth aspect of the present invention provides the analytical data producing device according to the tenth aspect, wherein:

the receiving means further receives device identification information that identifies a class of the measurement device and the measurement data associated therewith.

In this device, the analysis device further comprises the following means.

storage means for storing analysis methods of the measurement data for each class of the measurement device, determination means for determining the class of the measurement device based upon the measurement identification information, and selection means for selecting an analysis method corresponding to the class of the measurement device from amongst the stored analysis methods, and for applying the same to analysis of the measurement data.

This aspect produces the same functional effect as the eighth aspect.

The fourteenth aspect in the present invention provides the analytical data producing device according to the tenth aspect, further comprising:

results storage means for storing conditions on a contract relating to analysis of measurement data exchanged between a manager of the analytical data producing device and a manager of the measurement device, and usage results of the analytical data production device that the manager of the measurement device used, and determination means for determining items billed to the manager of the measurement device based on the contract conditions and the usage results.

This aspect produces the same functional effect as the ninth aspect.

The fifteenth aspect of the present invention provides a computer program product for an analytical data production, comprising:

connection means for connecting, via a network, a measurement device that conducts measurements for a subject's in vivo test and/or in vitro test and calculates measurement data, receiving means for receiving the measurement data from the measurement device via a network, analysis device for conducting an analysis of the measurement data, and calculating analytical data, and transmission means for transmitting, via the network, the analytical data to the measurement device.

The sixteenth aspect of the present invention provides a computer program product for an analytical data production, comprising:

connection means for connecting, via a network, a measurement device that conducts measurements for a subject's in vivo test and/or in vitro test and calculates measurement data, receiving means for receiving the measurement data from the measurement device via a network, analysis device for conducting an analysis of the measurement data, and calculating analytical data, and transmission means for transmitting, via the network, the analytical data to an output device that outputs analytical data.

This aspect produces the same functional effect as the fifteenth aspect.

The seventeenth aspect of the present invention provides a measurement device to be connected via a network to an analysis device, comprising:

measurement means for conducting measurements for a subject's in vivo test and/or in vitro test and for calculating measurement data, first connection means for connecting the measurement means to the analysis device, via the network, and first transmission means for transmitting the measurement data to the analysis device via the first connection means.

This device functions as the measurement device in the system discussed previously that employed the method of the first aspect.

The eighteenth aspect of the present invention provides a measurement device according to the seventeenth aspect, wherein:

the first transmission means associates a communication address of the measurement device with the measurement data and transmits the same.

This device corresponds to the measurement device in the fifth aspect.

The nineteenth aspect of the present invention provides a measurement device according to the seventeenth aspect, wherein:

first transmission means associates identification information of the subject and test items with the measurement data and transmits the same.

The twentieth aspect of the present invention provides a measurement device according to the seventeenth aspect, wherein:

the first transmission means associates device identification information that indicates the identity of the measurement device with the measurement data and transmits the same.

The twenty-first aspect of the present invention provides a measurement device according to the seventeenth aspect, further comprising:

output means for outputting analytical data obtained by analyzing the measurement data, second connection means for connecting the output means to the analysis device, receiving means for receiving from the analysis device analytical data obtained by analyzing the measurement data, and second transmission means for transmitting the analytical data received by the receiving means, via the second connection means, to the output means.

The twenty-second aspect of the present invention provides a measurement device according to the seventeenth aspect, further comprising:

output means for outputting analytical data from the analysis device.

This aspect corresponds to a construction in which the measurement device in the system is integral with the output device.

The twenty-third aspect of the present invention provides a computer program product, comprising:

measurement means for conducting measurements for a subject's in vivo test and/or in vitro test and calculating measurement data, first connection means for connecting the measurement means to an analysis device, via a network, that analyzes the measurement data, and first transmission means for transmitting the measurement data to the analysis device via the network.

The twenty-fourth aspect of the present invention provides an output device, comprising:

connection means for connecting a measurement device that conducts measurements for a subject's in vivo test and/or in vitro test and calculates measurement data, receiving means for receiving the measurement data from the measurement device via the connection means, and output means for outputting the measurement data.

The output device may receive analytical data from a server, and may receive analytical data from the measurement device.

The twenty-fifth aspect of the present invention provides an output device according to the twenty-fourth aspect, wherein:

the receiving means receives identification information and test items for the subject that is related to the measurement data, and the output device associates the subject's identification information and test items with the measurement data and outputs the same.

The twenty-sixth aspect of the present invention provides an output device, comprising:

connection means for connecting an analysis device that analyzes measurement data of a measurement device for a subject's in vivo test and/or in vitro test and calculates analytical data, receiving means for receiving the analytical data from the analysis device via the connection means, and output means for outputting the analytical data.

This aspect produces the same functional effect as the twenty-fourth aspect.

The twenty-seventh aspect of the present invention provides the output device according to the twenty-sixth aspect, wherein:

the receiving means receives identification information and test items for the subject that is related to the analytical data, and the output device associates the subject's identification information and test items with the analytical data and outputs the same.

This aspect produces the same functional effect as the twenty-fifth aspect.

The twenty-eighth aspect of the present invention provides a computer program product for an analytical data production, comprising:

connection means for connecting an analysis device that analyzes measurement data of a measurement device for a subject's in vivo test and/or in vitro test and calculates analytical data, receiving means for receiving the analytical data from the analysis device via the connection means, and output means for outputting the analytical data.

This aspect produces the same functional effect as the twenty-fourth aspect.

The twenty-ninth aspect of the present invention provides a computer program product for an analytical data production, comprising:

connection means for connecting a measurement device for a subject's in vivo test and/or in vitro test and calculates measurement data, analysis device for conducting an analysis of the measurement data, and calculating analytical data, receiving means for receiving the analytical data from the analysis device, and output means for outputting the analytical data.

This aspect produces the same functional effect as the twenty-eighth aspect.

From the following detailed description in conjunction with the accompanying drawings, the foregoing and other objects, features, aspects and advantages of the present invention will become readily apparent to those skilled in the art.

BRIEF DESCRIPTION OF THE DRAWINGS

FIG. 4 is a conceptual explanatory diagram of the information stored on a user DB;

FIG. 5 is a conceptual explanatory diagram of the information stored on a contract DB;

FIG. 6(a) is a conceptual explanatory diagram of original data transmitted to the analysis server from the measurement device;

FIG. 6(b) is an explanatory diagram showing one example of measurement data;

DETAILED DESCRIPTION OF THE PREFERRED EMBODIMENTS

Figure 1:
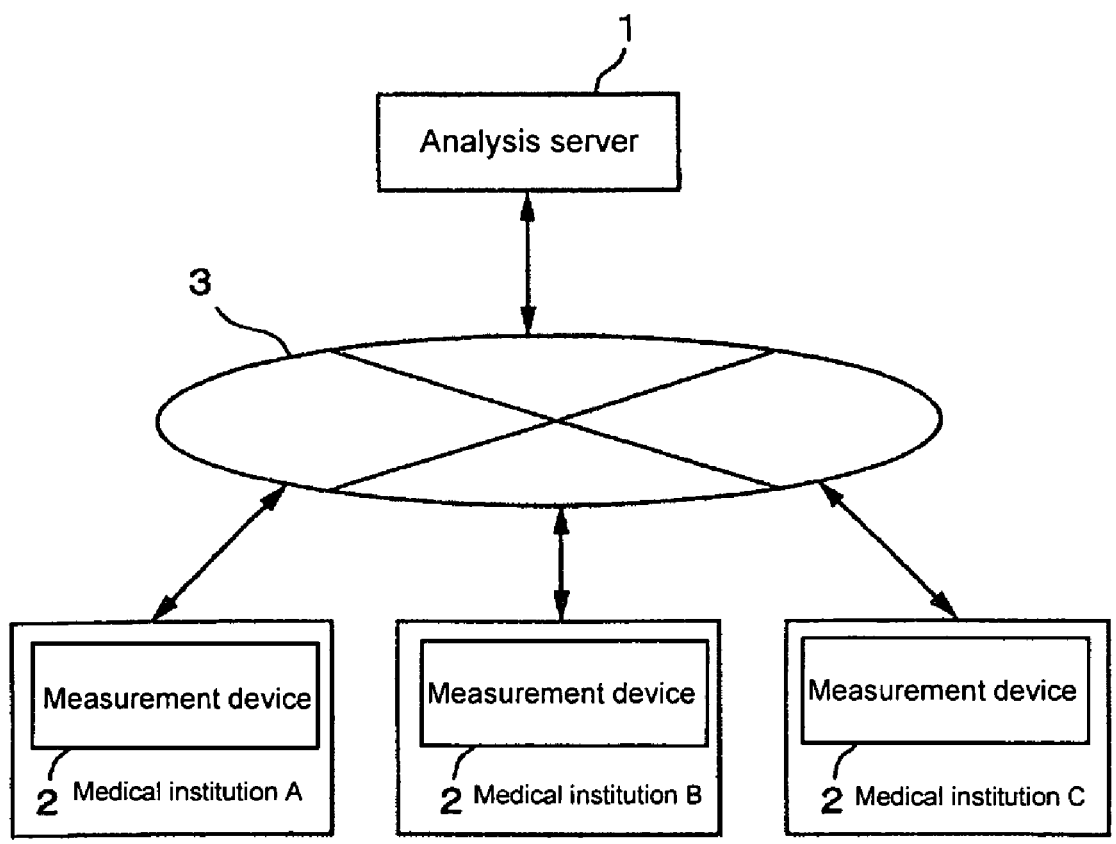
FIG. 1 is a conceptual diagram of the configuration of an analytical data production system.

FIG. 1 is a conceptual diagram showing an outline of the analytical data production system of the present invention. This system is composed of an analysis server 1 of an analytical data provider (hereinafter referred to as simply as "service provider"), user measurement devices 2, connected via a network 3 such as the Internet. The measurement device 2 is exemplified by a device of which constitution is modified from a Sysmex (K.K.) XE-2100 blood cell counter (hereinafter referred to as a blood cell counter), a device of which construction is modified from a Sysmex (K.K.) CA-1500 blood coagulation measuring device (hereinafter simply referred to as a blood coagulation measuring device), and a device of which construction is modified from a Sysmex (K.K.) PAMIA-50 immune aggregate measuring device, (hereinafter simply referred to as an immunaggregate measuring device). The construction of the measuring device will be discussed below.

In this analytical data production system, the measurement functions and analysis functions possessed by conventional testing devices are divided amongst the analysis server 1 and the measurement devices 2. Specifically, the analysis server 1 possesses an analytical function for each measurement device, and the measurement devices 2 possess measurement functions.

The analytical server 1 collects and analyzes measurement data from each measurement device 2, and returns analytical data (which is tantamount to an analytical result) to each user. The analytical data is purchased and provided to a user in accordance with a contract between a service provider and the user. The service provider and user will have previously entered into a contract relating to the contents of the analysis service and its cost.

Preferably, the analytical data providing service (hereinafter simply referred to as "analysis service") provides the measurement devices and the reagents free of charge, and provides analytical data in return for a fee. By doing so, the user can acquire the measurement devices and eliminate the burden of an initial investment. In addition, the service provider may only maintain the program used for analysis running in the analysis server 1. Each user can modify contract details as needed, can easily replace a measurement device, and can receive an analysis service adapted to changes in his needs.

First Embodiment

Next, an embodiment of the analytical data production system of the present invention will be described in detail.

(1) Construction (1-1) General Framework

Figure 2:
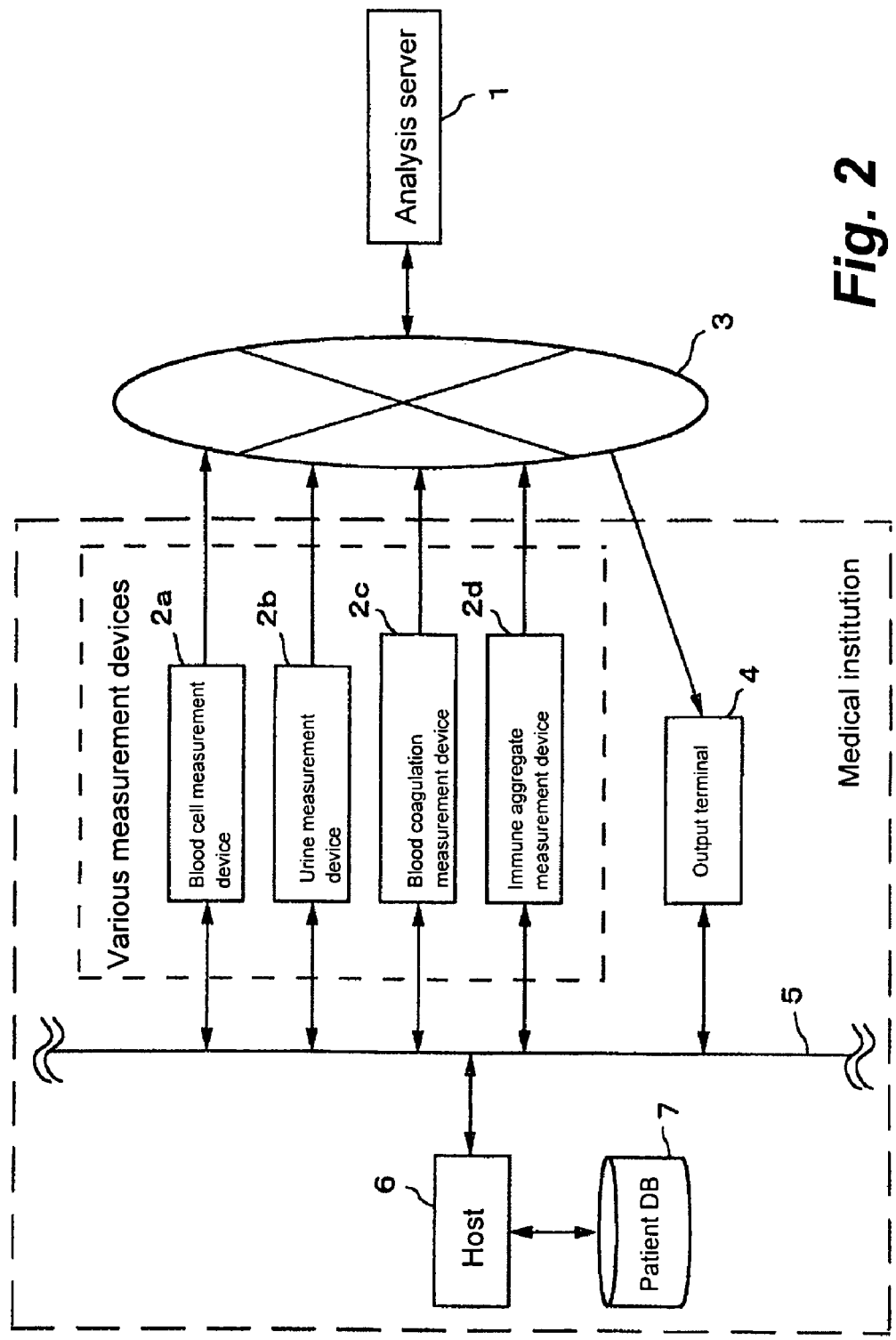
FIG. 2 is an overall configurational diagram of the analytical data production system according to a first embodiment.

FIG. 2 is an overall configurational diagram of the analytical data production system of the present embodiment. In addition, the relationship is between one user and the analytical server 1 in order to make the figure easier to understand. The user has a plurality of measurement devices 2a, 2b, 2c and 2d which are capable of being connected to a network 3, and an output terminal 4. The measurement devices 2a to 2d and the output terminal 4 are connected to a host 6 by means of a user network 5 such as a LAN or the like. The host 6 controls the measurement devices 2 and the output terminal 4, and information relating to patients' test results, medical histories, medication histories and the like are stored in patient database 7 (hereinafter simply referred to as "patient DB").

(1-2) Construction of Analysis Server 1

Figure 3:
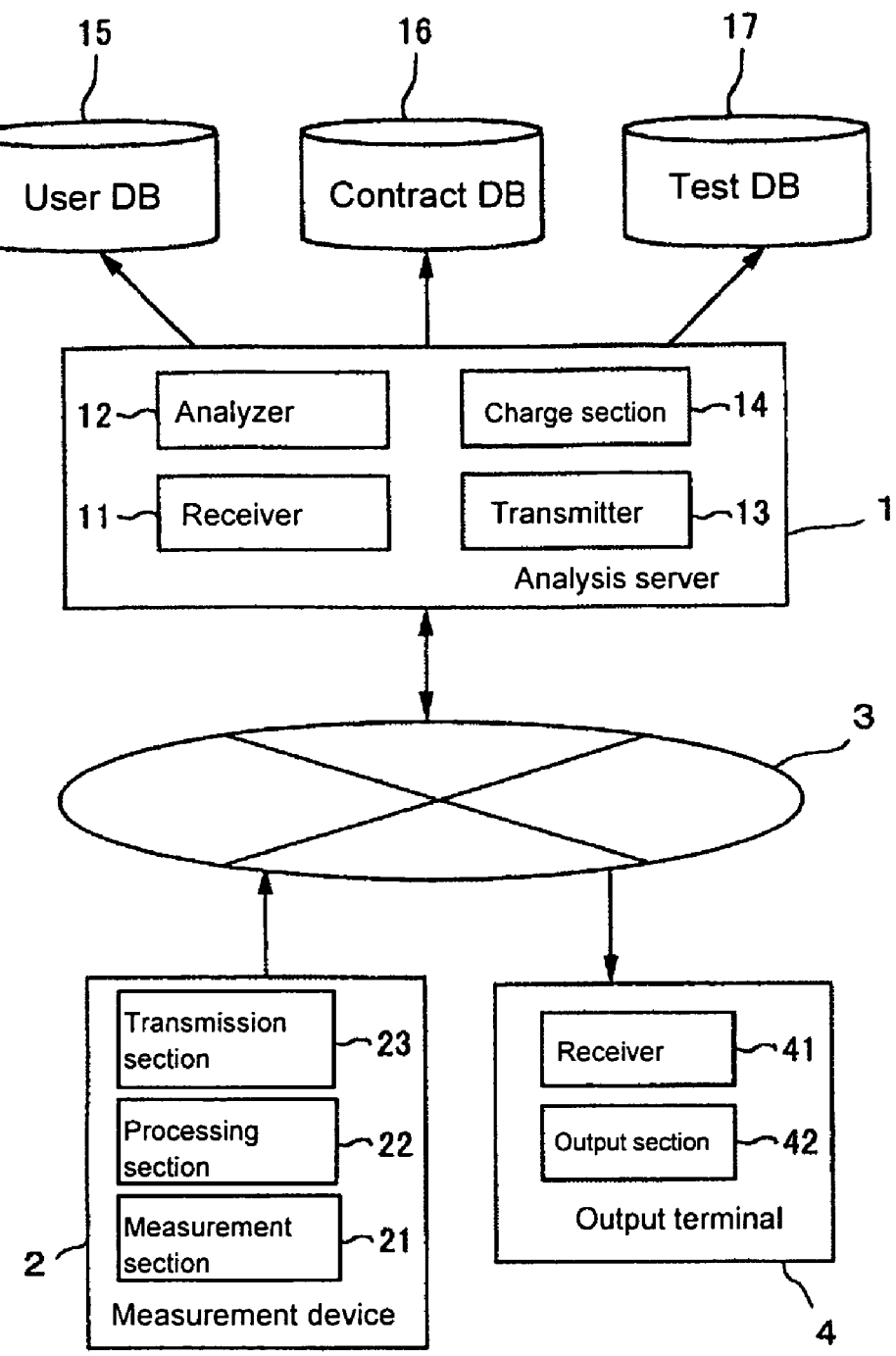
FIG. 3 is a block diagram of the functions of an analysis server and measurement device.

FIG. 3 is a block diagram describing the details of the functions of the measurement device 2 and the output terminal 4. In this figure, the measurement device 2 is exemplified by a blood coagulation measurement device. The analysis server 1 can be effectuated by using a personal computer and the like, and has a first receiving unit 11 that receives data from the measurement devices 2, an analyzing unit 12 that analyzes the measurement data received, a second transmitting unit 13 that transmits the analytical data to the output terminal 4, and a charge unit 14 that calculates the charge for each user. The analyzing unit 12 selects the optimal analysis program from a program database 18 (discussed below) according to the type of measurement data transmitted, and performs an analysis of the measurement data.

In addition, the analysis server 1 has a user database 15 (hereinafter simply referred to as "user DB"), a contract database 16 (hereinafter simply referred to as "contract DB"), a test database 17 (hereinafter simply referred to as "test DB"), and a program database 18 (hereinafter, simply referred to as "program DB") in its hard disk. A user's actual use of the analysis service is stored in user DB 15. The results of each user's actual usage of analysis service are stored in user DB 15. The contract details of each user and the service provider are stored in contract DB 16. Details on user DB 15 and contract DB 16 are discussed below. Test DB 17 can be provided according to need. This DB stores measurement data received by analysis server 1 and the analytical data. In the event that the service provider is the provider of both the measurement devices and the analysis programs, it can make use of the stored data in order to further correct and improve the measurement and analytical abilities of its products. Analysis programs in order to analyze measurement data are stored in program DB 18. Each program can be associated with a class of measurement device that measures the measurement data, a version of a measurement program installed in a measurement device, and the like.

(1-3) Construction of the Measurement Device

The measurement device 2 may be a device that has measurement functions for in vitro tests and in vivo tests, and are not particularly limited thereby. In order to simplify the description, a blood coagulation measurement device will be used as an example of the measurement device in the present embodiment, and an explanation will be provided below.

(1-3-1) An Example of a Conventional Testing Device that is the Basis for the Measurement Device of the Present Invention.

Figure 18:
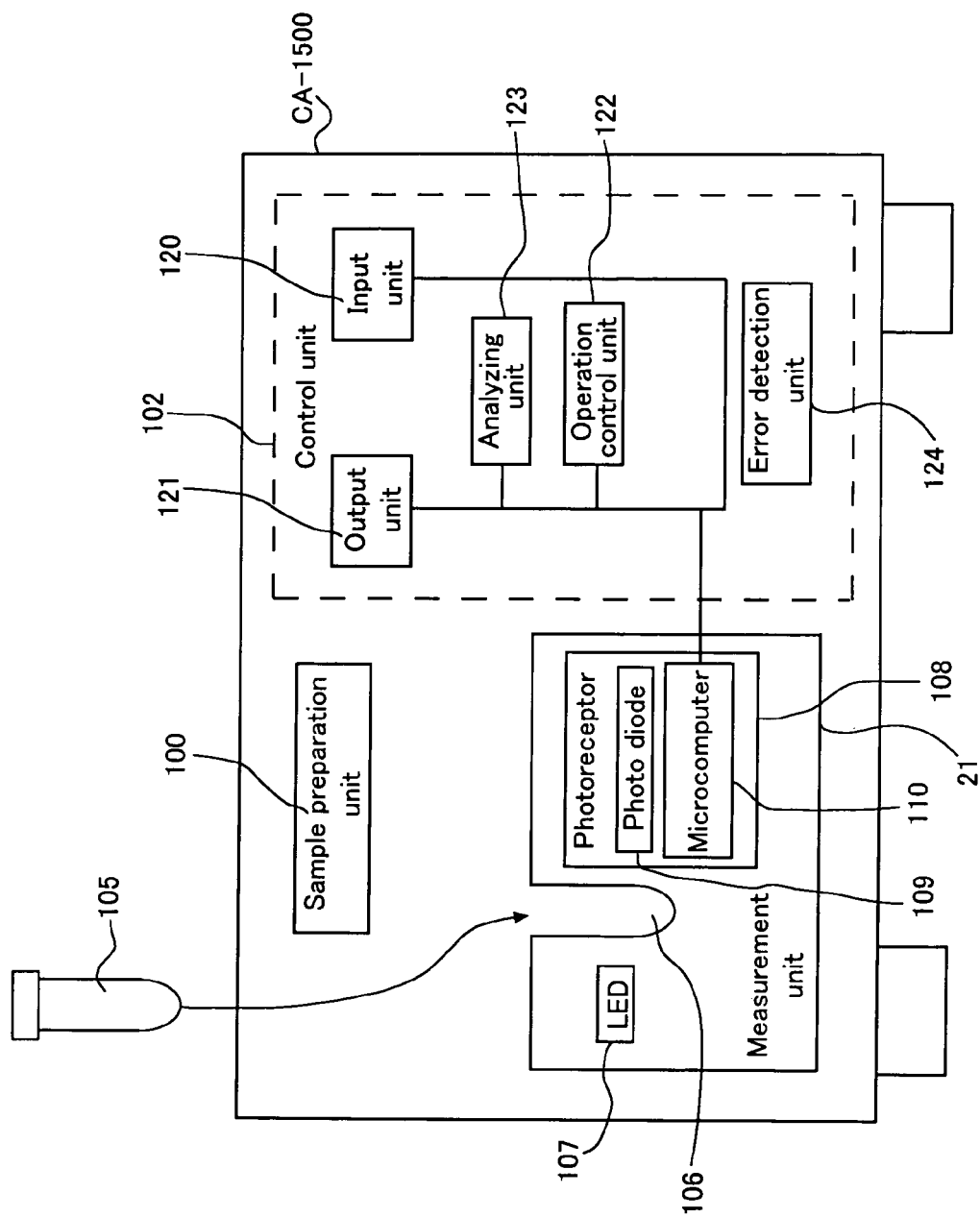
FIG. 18 is a configurational diagram of a CA150 that forms the basis for the measurement device (blood coagulation measurement device) in the system of FIG. 2.

FIG. 18 shows the construction of a Sysmex (K.K.) CA-1500 testing device that is the basis of the blood coagulation measuring device used as an example of the measuring device of the present invention. The CA-1500 consists mainly of a sample preparation unit 100, a measurement unit 21, and a control unit 102.

The sample preparation unit 100 consists of a liquid drawing device, a reagent drawing device, a cuvette transfer device, and the like, the operation of which is controlled by the control unit 102. The sample preparation device 100 draws blood from a blood-collecting vessel, injects the blood and a reagent into a clean container known as a cuvette 105 (hereinafter referred to as a cuvette), and moves the cuvette 105 to the measurement unit 21. Details on the cuvette 105 are disclosed in U.S. Pat. No. 5,658,532. Details on the reagent are disclosed in U.S. Pat. No. 5,928,949.

The measurement unit 21 includes a cuvette setting section 106 to which the cuvette 105 is set, a laser diode (LED) 107 positioned on both sides of the cuvette setting section 106, and an optical receptor 108. The optical receptor 108 consists of a photo diode 109, and a microcomputer 110. The intensity of an electric current obtained from the photodiode 109 is converted to a numerical value to become measurement data, and microcomputer 110 transmits this measurement data to the control unit 102 over fixed intervals of time. The intensity of a light received by the photodiode 109 is converted to a numerical value to become measurement data, and the measurement unit 21 transmits this measurement data to control unit 102 over fixed intervals of time.

The control unit 102 consists mainly of an input unit (touch panel) 120, an output unit (liquid crystal display) 121, an operation control unit 122, an analyzing unit 123 and an error detection unit 124. The operation control unit 122, the analyzing unit 123 and the error detection unit 124 consist mainly of a CPU, ROM, RAM and a hard disk. An operation control program that controls the operation of the sample preparation unit 100 and the measurement unit 21 is installed in the ROM of the operation control unit 122. An analysis program is installed in the ROM of the analyzing unit 123. The analysis program calculates analytical data based on the intensity of the light (measurement data) obtained from the measurement unit 21 and the data input by the user from the input unit 120, and outputs the analytical data to the output unit 121. An error detection program is installed in the ROM of the error detection unit 124. The error detection program displays an error message in the output unit 121 in the event that the amount of blood is insufficient, or that blood cannot be properly drawn or measured due to an abnormality in the sample preparation unit 100.

(1-3-2) An Example of the Measurement Device of the Present Invention

Figure 19:
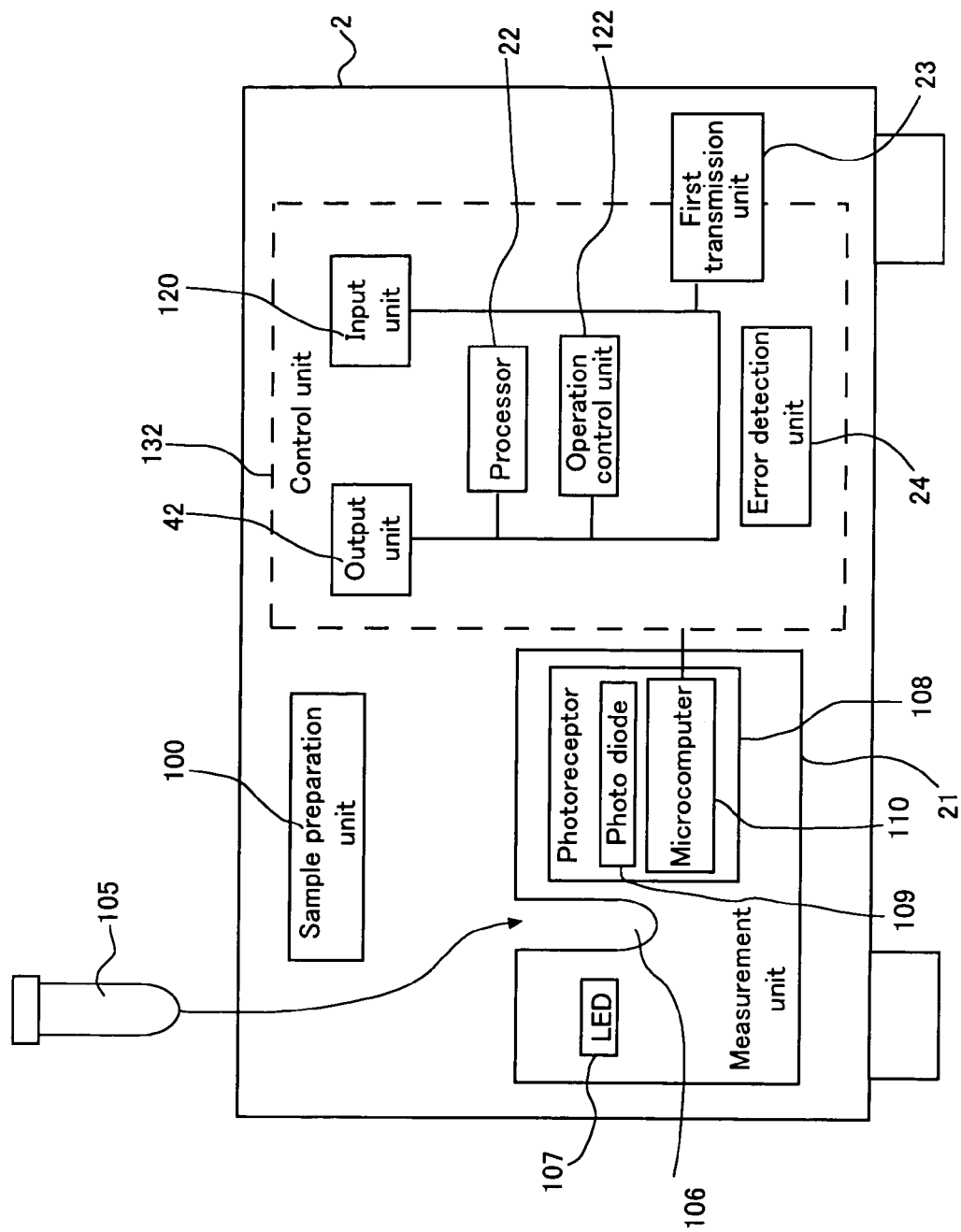
FIG. 19 is an explanatory diagram showing an example of the configuration of the measurement device in the system of FIG. 2.

FIG. 19 shows a detailed construction of a blood coagulation measurement device 2 that is a modification of the aforementioned CA-1500, which can be used as a measurement device 2 of the present invention. In the figure, the elements that have the same function and construction of those in FIG. 18 are referred to with the same reference numerals.

Both the sample preparation unit 100 and the measurement unit 21 have the same function and construction as those described above. Control unit 132 consists of an input unit (touch panel) 120, output unit (liquid crystal display) 42, operation control unit 122, processor 22, a first transmission unit 23 and an error detection unit 24. The operation control unit 122, the processor 22 and the error detection unit 24 mainly consist of a CPU, ROM, RAM and a hard disk. The first transmission unit 23 mainly consists of a CPU, ROM, RAM, a hard disk and a modem.

An operation control program that controls the operation of the sample preparation unit 100 and the measurement unit 21 is installed in the ROM of the operation control unit 122 (the same program used in the CA-1500 can be used here).

A processing program is installed in the ROM of the processor 22. The processing program produces original data (discussed below) based upon measurement data obtained from the measurement unit 21 and data inputted by the user from the input unit 120.

A transmission program is installed in the ROM of the first transmission unit 23. The transmission program transmits original data to analysis server 1 via the modem and the network 3.

An error detection program is installed in the ROM of the error detection unit 24. The error detection program stops the generation of original data in the processor 22 in the event that the amount of blood is insufficient, or that blood cannot be properly drawn or measured due to an abnormality in the sample preparation unit 100. This is in order to avoid the inconvenience of charging the user although he was not able to obtain analytical data. The error detection unit 24 may be constructed such that it stops the generation of original data in the processor 22 and displays an error message in the output unit 42.

In the event that the analytical data production system of the present invention is constructed such that the measurement device 2 receives analytical data from the analysis server 1, the measurement device 2 may be equipped with a receiver (not shown in the figures) that receives analytical data and outputs it to the output unit 42. The receiver can be constructed to employ a CPU, ROM, RAM, hard disk, and modem. A receiving program that receives analytical data transmitted from the analysis server 1 via the modem and displays analytical data in the output unit 42 is installed in the ROM of the receiver.

It is not always necessary to equip the measurement device 2 with the analyzing unit 123 provided in the CA-1500. If the analyzing unit 123 is provided therein, the analyzing unit 12 provided in the analysis server 1 can be made to have greater analytical abilities. This can increase the desire of a user to subscribe to the analysis service.

(1-4) Construction of the Output Terminal

The output terminal 4 has a second receiving unit 41 that receives analytical data from the analysis server 1, and an output unit 42 that outputs analytical data to a display, a printer, or the like. The output unit 42 is capable of operating output programs for a plurality of analysis programs. The output terminal 4 may be effectuated on the same computer as the measurement device 2, or may be effectuated on a separate computer.

(2) Database (2-1) User DB

FIG. 4 is a conceptual explanatory diagram of the information stored in user DB 15. In this example, a user ID, user name, contact person, contract details, and actual usage are stored in the user DB.

"User ID" is information for identifying users on the present system. A user ID is assigned to (is associated with) a user, for example, at the time of contracting between the service provider and the user.

"User name" is the name of the medical institution that uses the service, and the "contact person" is the name and department of the responsible party concerned with the present analysis service.

"Contract details" is information that identifies the user with his contract details stored in contract DB 16.

"Actual usage" is the use status of the user's analytical service during a fixed period of time, for example, one month. Both the analysis service ID and the number of times the analytical service has been used are stored. The analysis service ID is an ID for identifying the test items, and the test items that are included in each ID are described in contract DB 16.

Information other than that illustrated here can be stored in user DB 15 according to need.

(2-2) Contract DB

FIG. 5 is a conceptual explanatory diagram of the information stored in contract DB 16. In this example, the contract details, analysis service ID, test items, basic contract flag, basic unit cost, and maximum number of uses are stored in contract DB 16.

"Contact details" is identical to the "contract details" used in the aforementioned user DB, and is an identifier for the contract with the user. For example, the contract details of "Sysmex Hospital" in FIG. 4 is identified as "123-4567".

The analysis service ID and the test items identify the details of the analysis service that the user has contracted for. Specifically, a group of test items or one test item is associated with an analysis service ID. For example, in the figure "BASIC" and "C001" indicate analysis of each test item APTT, PT, and Fbg. Further, "C002" indicates analysis of TTO.

"Basic contract flag" indicates whether or not the test items are included in a basic contract. With coagulation measurements, APTT, PT, and Fbg are the test items that are most commonly performed. Generally, the number of measurement for these items for a month is less than 100 times. Because of this, in FIG. 5 these are included in the basic contract, and other tests are not included in the basic contract. Of course, the basic contract setup can take various forms other than this. In addition, in the present example, a basic contract that includes the analysis service adds value and provides a relatively less expensive analysis service when compared with an analysis service outside the basic contract.

"Basic unit cost", for example, is the basic monthly fee when the user is billed for his service use in one month increments, or is the unit cost for analysis per specimen. "Maximum number" is the number of specimens that the analysis service provides at the price set by the basic unit cost. In this example, the method of billing for the same tests under "BASIC" and "C001" is different. In other words, a monthly fee of 15,000 yen provides up to 100 specimens, and each test in excess of this is billed at 200 yen. In addition, TTO is billed at 450 yen for each test, which is relatively more expensive than a basic contract item. This is because the reagents used for the measurement of TTO are more expensive than the reagents used in the measurement of APTT, PT, and Fbg.

Information other than that exemplified here can be stored in contract DB 16 according to need.

(3) Data

Next, the data that is transmitted and received between analysis server 1 and measurement devices 2 will be explained in detail.

(3-1) Original Data Transmitted from the Measurement Device to the Analysis Server FIG. 6(*a*) shows a conceptual explanatory diagram of the information included in the original data transmitted from the measurement device 2 to analysis server 1. Below, each item that contains this data will be described.

(a) User ID

User ID is information that identifies the user that is transmitting measurement data. In the event that there is a plurality of users that can connect to the analysis server 1, a user ID is essential information.

(b) Specimen ID is essential information for allowing the user to be associated with the specimen. In this example, the specimen ID among each user are used as is for the specimen ID of the original data. This is because the specimens can be identified even in analysis server 1 by associating a user ID with a specimen ID.

(c) Device ID

Device ID is information used to identify the measurement devices belonging to the user. If the device ID and analytical data are associated with each other and stored in test DB 17, it is preferable that the disposition of the analytical data of each measurement device can be ascertained.

(d) Analysis Order

Analysis order is identifying information ascribed to each original data, in order to identify the original data in each measurement device that is transmitted to analysis server 1. For example, the date and time, a serial number, or the like can be used for the analysis order. The analysis order is not essential, however it is information that can identify transmission data other than by the user ID or specimen ID, and is thus preferably used.

(e) Sample Classification

Sample classification indicates information that identifies the type of specimen, for example whole blood, blood plasma, urine, bone marrow, or the like. In the present embodiment, the sample classification is blood plasma because the measurement device is a blood coagulation measurement device. Further, in original data that include in vivo test measurement data, information indicating the physical classification of the data, such as human, dog, cat or the like, is indicated as a sample classification.

(f) Test Item

"Test item" is the name of the item that the user is trying to test. The example in FIG. 6 shows the case where only a PT test is requested. Further, in the event that, for example, the three basic coagulation tests APTT, PT and Fbg are requested, the test items will be "APTT, PT, Fbg". Furthermore, if, for example, the contract entered into indicates that "only PT is to be measured for all specimens", then the transmission of the test items can be omitted.

(g) Measurement Items

Measurement items are items that are needed in order to determine the test results of a specimen. There are cases in which measurement data obtained from a plurality of measurement units are needed in order to provide the test results for one test item. In the event that a device of which construction is modified from Sysmex (K.K.) XE-2100 blood cell counter is used as the measurement device 2, and the test item is the 5 classes of white blood cells (lymphocytes, monocytes, neutrophils, eosinophils, and basophils), the test results provided are dependent upon both the measurement data on the lymphocytes, monocytes, neutrophils, and eosinophils obtained by the white blood cell 4 class measurement unit, and the measurement data on the basophils obtained by the basophil measurement unit. In this situation, the test item is the 5 classes of white blood cells, namely, lymphocytes, monocytes, neutrophils, eosinophils, and basophils, and the measurement items are the measurement of 4 classes of white blood cells and the measurement of basophils. Conversely, there are also cases in which a plurality of test results can be provided from one measurement data. For example, in the aforementioned blood cell counter, both red blood cells and blood platelets can be analyzed in the red blood cell measurement unit. In this situation, even though the test items are red blood cells and blood platelets, the measurement item is only red blood cells. In the original data illustrated in FIG. 6(*a*), the test item and the measurement item are both PT. The modifications in construction from the XE-2100 to a blood cell counter that can be used in the present invention can be effectuated in the same manner as the modifications in construction from the CA-1500 (previously discussed) to a blood coagulation measurement device that can be used in the present invention.

(h) Device classification

The device classification indicates the type of measurement device that measured the specimen or the changes in the body, for example, the product number, model, and the like.

It is information needed for the analysis of the measurement data.

(i) Device version

The device version indicates the version of the measurement program that runs in the measurement device. Even if it is the same class of device, if the version of the measurement program is different, there will be situations in which the analysis program is different. The analysis program used for analysis of the measurement data can be determined by specifying the class of device with the device version.

(j) Reply Address

The reply address is the communication address on the device network to which the analytical data is to be sent.

In this example, the e-mail address of the user's output terminal 4 indicates the reply address. As discussed below, the e-mail address of the measurement device 2 can also be used as the reply address.

In the event that the measurement device 2 and the analysis server 1 are connected one-to-one, the analysis server 1 will end up transmitting analytical data to only one measurement device 2. In this situation, it is not necessary to transmit the reply address from the measurement device 2 to the analysis server 1. This is because the reply address of the measurement device 2 is pre-stored in the analysis server 1, and the analytical data should be always transmitted to the reply address.

Information regarding a user such as user ID, device ID and the like, and the reply address, can be correlatively stored in the analysis server 1. In this way, if the analysis server 1 receives the user ID, the measurement ID, and the like from the measurement device 2, it can specify the reply address to which the analytical data is to be transmitted.

(k) Correction Value

The correction value is a datum or data for protecting against variance appearing even though the same sample is measured by the measurement device 2. In fact, by combining the measured data and the correction value, accurate analysis becomes possible. The correction value is setup only in an arbitrary measurement device, due to differences in the state of the measurement device, the measurement reagent, and the like.

(l) Measurement Data

Measurement data indicate data measured by the measurement device 2.

FIG. 6(*b*) is an explanatory diagram showing an example of measurement data when the measurement device 2 is a blood coagulation measurement device. Measurement data are a combination of measurement time (seconds) and the intensity of the scattered light in this period (%). The intensity of the scattered light (%) is a numerical value converted by microcomputer 110 from the intensity of the electrical current obtained by photodiode 109.

(3-2) Working Data Transmitted to Output Terminal From the Analysis Server

Figures 7, 8:
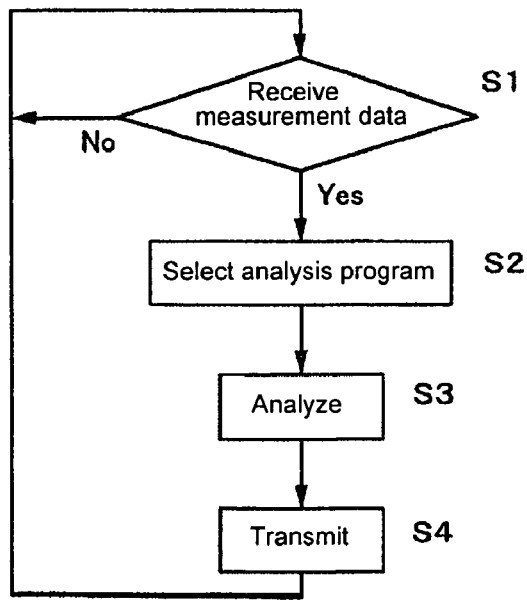
FIG. 7 is a conceptual explanatory diagram of the working data transmitted to an output terminal from the analysis server.
FIG. 8 is a flowchart showing the flow of the analysis process.

FIG. 7 is a conceptual explanatory diagram of the working data that are transmitted to the output terminal 4 from the analysis server 1. In this figure, the user ID, specimen ID, device ID, analysis order, and device classification are the same as those discussed above. Analytical data indicates the analytical data of the measurement data. In the case of the aforementioned PT measurement, the time change of the intensity of scattered light is analyzed, and the number of seconds of coagulation time (protothrombin time or PT) is indicated. The method of calculating the number of seconds of PT is discussed below.

(4) Process Flow

Next, in the analytical data production system having the aforementioned configuration, the process flow that takes place in the analysis server 1 will be explained in detail.

(4-1)

FIG. 8 is a Flowchart That Shows the Flow of the Analysis Process that Takes Place by the Analysis Server 1.

Step S1 and S2: The measurement device 2 measures the specimens set in the measurement unit 21 one by one, and transmits original data to the analysis server 1. The analysis server 1 selects an analysis program to be used for analyzing the measurement data, depending upon the sample classification, measurement item, device classification, and the device version in the original data received.

Step S3: Next, the analysis server 1 uses the analysis program selected to analyze the measurement data.

Figure 9:
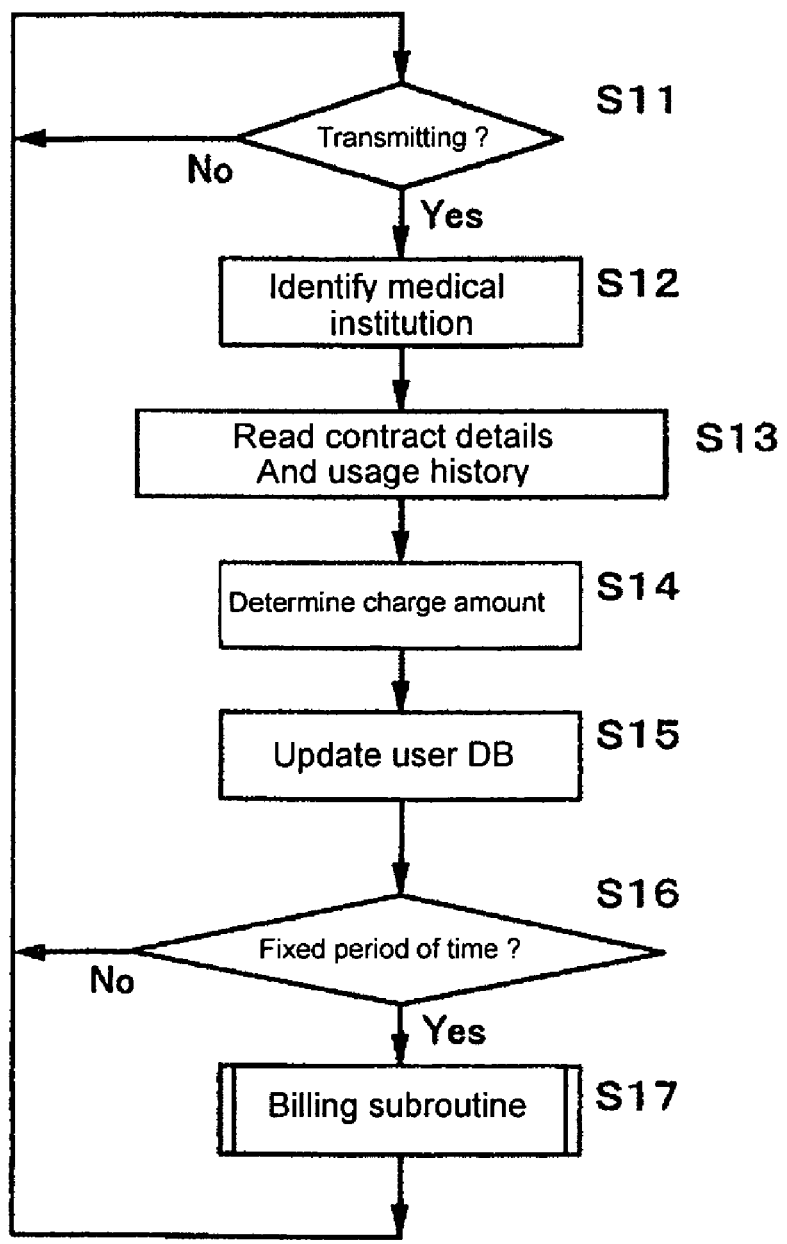
FIG. 9 is an explanatory diagram showing one example (analysis of PT) of the analysis process.

Here, the calculation of the number of seconds of PT will be discussed in detail as an example of the analysis of the measurement data. The analysis server 1 that obtained the measurement data shown in FIG. 6(*b*) produces a graph based on the measurement data, which is illustrated in FIG. 9. Moreover, the analysis server 1 calculates the time when light scattering intensity=50% from the above-mentioned graph. In the example in FIG. 9, because this time is 11 seconds, the analytical data=11 seconds.

Meanwhile, in the clinical testing industry of today, it is common to use the time when light scattering intensity=50% as the blood coagulation time. However, times change, and thus there may be a time when, for example, it will be common to use the time when light scattering intensity=60% as the blood coagulation time. Even in this type of situation, if the system of the present invention is employed, it will not be necessary for the user to effectuate a modification of the analysis program, because analysis server 1 is with the service provider, and thus, the situation can be dealt with quickly.

Step 4: The analysis server 1 produces working data that include analytical data and the aforementioned predetermined data, and transmits them to the reply addressee. This reply address is included in the original data. Sometimes one working data set includes analytical data on a plurality of test items, and sometimes is transmitted per test item.

The analysis server 1 repeats the process of Steps S2 to S4 each time it receives original data.

(4-2) Charge Process

Figure 10:
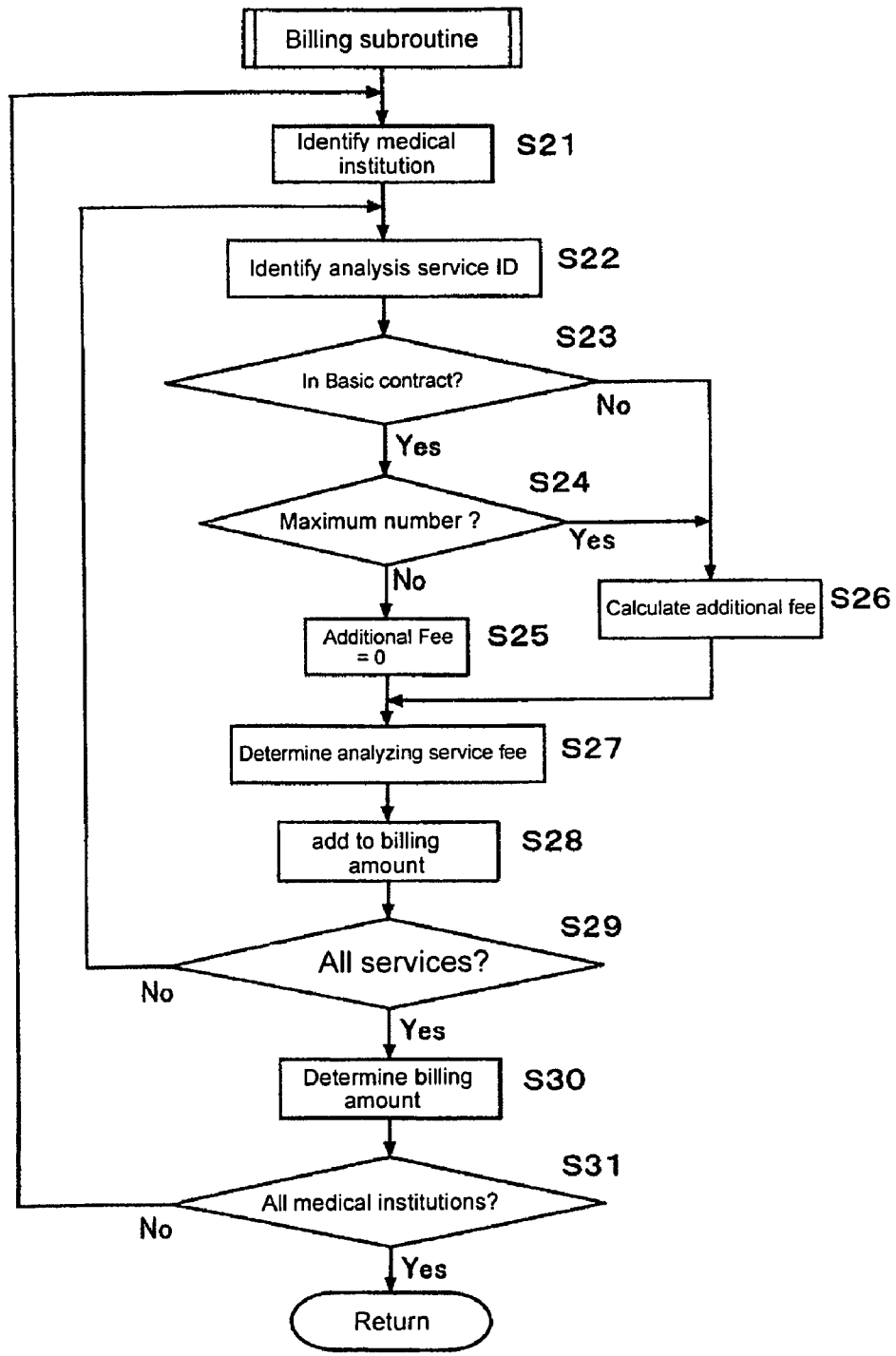
FIG. 10 is a flowchart showing the flow of the charge process.

FIG. 10 is a flowchart showing the flow of the charge process that takes place by means of the analysis server 1.

Step S11: When the analysis server 1 analyzes the measurement data and transmits the analytical data, the following charge process takes place.

Step S12: Based on the user ID included in the working data, the analysis server 1 specifies a user to be charged.

Step S13: The analysis server 1 refers to contract DB 16, and reads out the user's contract as the charge object. Next, the analysis server 1 reads out the user's actual service usage as the charge object from user DB 15.

Step S14: Based on the test items in the working data, the actual usage, and the contract, the analysis server 1 determines to which analysis service ID the transmitted analytical data corresponds. For example, a case in which the analytical data illustrated in FIG. 7 is determined will be explained based on the actual usage in the aforementioned FIG. 4 and the contract details in FIG. 5. Because the only test item in the analytical data transmitted is PT, the analysis service ID can be determined as follows. With regard to user ID "U-Sysmex", the number of analyses of the three basic items (APTT, PT, and Fbg) exceeds the monthly maximum of 100 specimens. Thus, from amongst the analysis service IDs that the test item PT corresponds to, the aforementioned analytical data is determined to be "C001".

As a further example, consider a situation in which the test items of analytical data transmitted are APTT, PT, Fbg, and TTO. Similarly, based on the above mentioned FIGS. 4 and 5, regarding the basic 3 items of the analytical data transmitted, the analysis service ID is "C001". Further, with TTO, the analysis service ID is "C002" regardless of the number of specimens. In other words, the analysis service ID that the transmitted analytical data corresponds to is determined to be "C001" and "C002".

Step S15: The analysis server 1 updates user DB 15. Specifically, the number of analyses of the analysis service ID that the analytical data corresponds to is incremented. For example, in the event that analytical data corresponds to "C001", the number of analyses of "C001" increases by one. In the event that the analytical data corresponds to "C001" and "C002", the number of uses corresponding to each ID increases by one. The analysis server 1 repeats the process of Steps S12 to S15 each time it transmits working data.

Step S16 and S17: In addition, the analysis server 1 adds up the total amount of charges of each user during a fixed interval, for example, one month, and a billing process then takes place.

(4-3) Billing Process Flow (4-3-1) Summary of the Billing Process Flow

Figure 11:
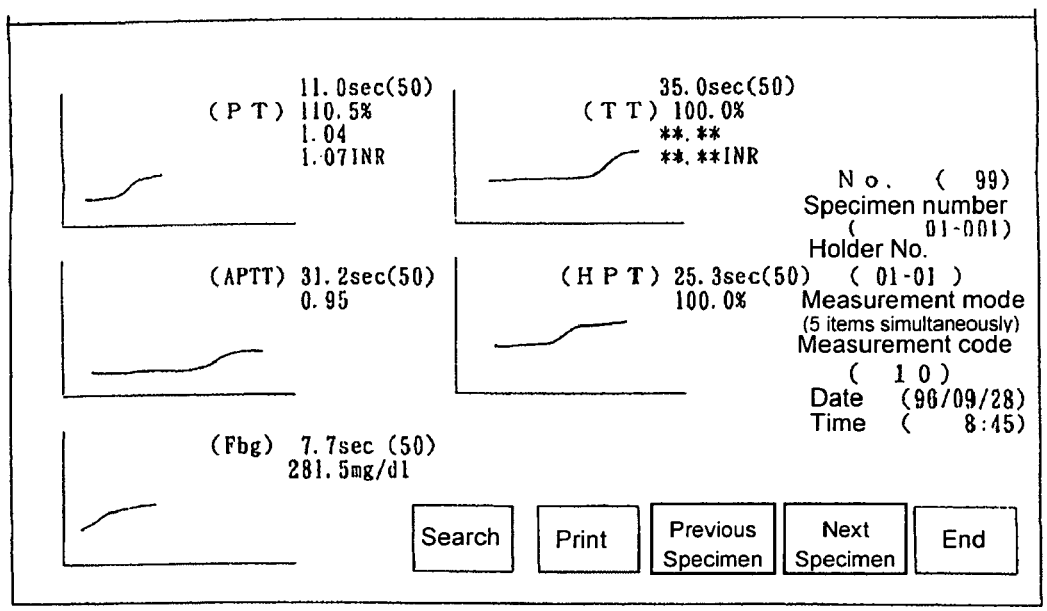
FIG. 11 is a flowchart showing the flow of the billing process.

FIG. 11 is a flowchart showing the flow of the billing process that analysis server 1 performs during each fixed interval. In order to simplify the explanation, the billing process will occur in one-month intervals.

Step S21: The analysis server 1 specifies any user registered as the calculation object of the amount billed. Further, a variable TA that indicates the total amount billed=0.

Step S22: The analysis server 1 refers to user DB 15, and specifies any analysis service ID described in the calculation object of the user's actual usage as a calculation object.

Step S23: The analysis server 1 refers to contract DB 16, and determines whether or not the analysis service ID specified is included in a basic contract. If "Yes", then the analysis server 1 moves to Step S24. If "No", then the analysis server 1 moves to Step S25 (discussed below), and calculates additional charges.

Step S24: Regarding an analysis service ID included in a basic contract, the analysis server 1 adds the basic unit price of that analysis service ID to total amount billed TA.

Step S25 and S26: With an analysis service ID not included in a basic contract, the analysis server 1 multiplies the unit price of that the analysis server ID by the number of times it was used, and adds this amount as an additional charge (S25). The basic unit cost is determined by referring to contract DB 16. In addition, analysis server 1 adds the additional charges calculated to the total amount billed TA (S26).

Step S27: With all analysis service IDs that correspond to the user as a calculation object, the analysis server 1 determines whether or not the use charges have been calculated. If "Yes", the analysis server 1 moves to Step S28. If "No", the analysis server 1 returns to Step S22, and calculates the use charges for the next analysis service ID. In other words, the analysis server 1 repeats Steps S22 to S26, calculates the use charges for all analysis service IDs that were used, and determines the total amount billed TA.

Step S28: The analysis server 1 associates total amount billed TA with the user, and temporarily holds it. Although not shown in the figure, total amount billed TA may be written in the user DB.

Step S29: The analysis server 1 repeats the process of the aforementioned Steps S21 to S28 for all users, and determines the amounts to be billed per month.

Afterward, the analysis server 1 may also run predetermined billing processes according to need. For example, it can perform such tasks as issuing a bill for each user, run a process for automatic deduction from a bank, and the like.

(4-3-2) Specific Example of the Flow for Determining the Total Billed Amount

For example, in the case of a user's actual usage for a particular month shown in the aforementioned FIG. 4, and the contract details shown in the aforementioned FIG. 5, the amount of each analysis service ID and the total amount billed will be as follows.

Step S21: The analysis server 1 specifies Sysmex Hospital as the calculation object of the billed amount according to the user ID and the user name. The initial value of variable TA that indicates the total amount billed is "0".

Step S22: The analysis server 1 refers to user DB 15, and from amongst the analysis service IDs that are described in the actual usage of Sysmex Hospital, specifies "BASIC" as the calculation object.

Step S23: The analysis server 1 refers to contract DB 16, and determines whether or not the analysis service ID "BASIC" specified at Step S22 is included in a basic contract. Because "BASIC" is included in a basic contract, analysis server 1 determines the answer to be "Yes", and moves to Step S24.

Step S24: The analysis server 1 adds the 15,000 yen basic unit cost of "BASIC", to total amount billed TA=0, and thus TA=15,000.

Step S27: The analysis server 1 determines whether or not the usage charges for all analysis service IDs corresponding to Sysmex Hospital have been calculated. Here, because "BASIC" is the only usage charge that has been calculated from amongst the analysis service IDs, the analysis server 1 determines the answer to be "No", returns to Step S22, and calculates the usage charge for the next analysis service ID.

Step S22: The analysis server 1 refers to user DB 15, and specifies "C001" as the calculation object from amongst the analysis service IDs that are described in the actual usage of Sysmex Hospital.

Step S23: The analysis server 1 refers to contract DB 16, and determines whether or not the analysis service ID "C001" specified at Step S22 is included in the basic contract. Because "C001" is not included in the basic contract, analysis server 1 determines the answer to be "No", and moves to Step S25.

Step S25 and S26: The analysis server 1 multiplies the 200 yen basic unit cost of "C001" by the number of uses 60, and calculates 200 yen×60 yen=12,000 yen as the additional charge. The basic unit cost is determined by referring to contract DB 16. In addition, the analytical server 1 adds the 12,000 yen additional charge to total amount billed TA=15000, and thus total amount billed TA=27,000.

Step S27: The analysis server 1 determines whether or not the usage charge calculated for all analysis service IDs correspond to Sysmex Hospital. Here, amongst the analysis service IDs, the usage charges for "BASIC" and "C001" have been calculated, but the usage charge for "C002" has not been calculated. Because of this, the analysis server 1 determines the answer to be "No", returns to Step S22, and calculates the usage charge for the next analysis service ID.

Step S22: The analysis server 1 refers to user DB 15, and specifies "C002" as the calculation object from amongst the analysis service IDs described in the usage charges of Sysmex Hospital.

Step S23: The analysis server 1 refers to contract DB 16, and determines whether or not the analysis service ID "C002" specified in Step S22 is included in the basic contract. Because "C002" is not included in the basic contract, the analysis server 1 determines the answer to be "No", and moves to Step S25.

Step S25 and S26: The analysis server 1 multiplies the 450 yen basic unit cost of "C002" by the number of uses 37, and calculates 450 yen×37=16650 as an additional charge. The basic unit cost is determined by referring to contract DB 16. In addition, the analysis server 1 adds the 16,650 yen additional charge to the total amount billed TA=27000, and thus total amount billed TA=43,650.

Step S27: The analysis server 1 determines whether or not the usage charge for all analysis service IDs that correspond to Sysmex Hospital have been calculated. Here, because the usage charges for all of the analysis service IDs have been calculated, the analysis server 1 determines the answer to be "Yes", and moves to Step S28. The total amount billed to Sysmex Hospital is 43,650 yen/month.

(5) Analytical Data Display Example

Figure 12:
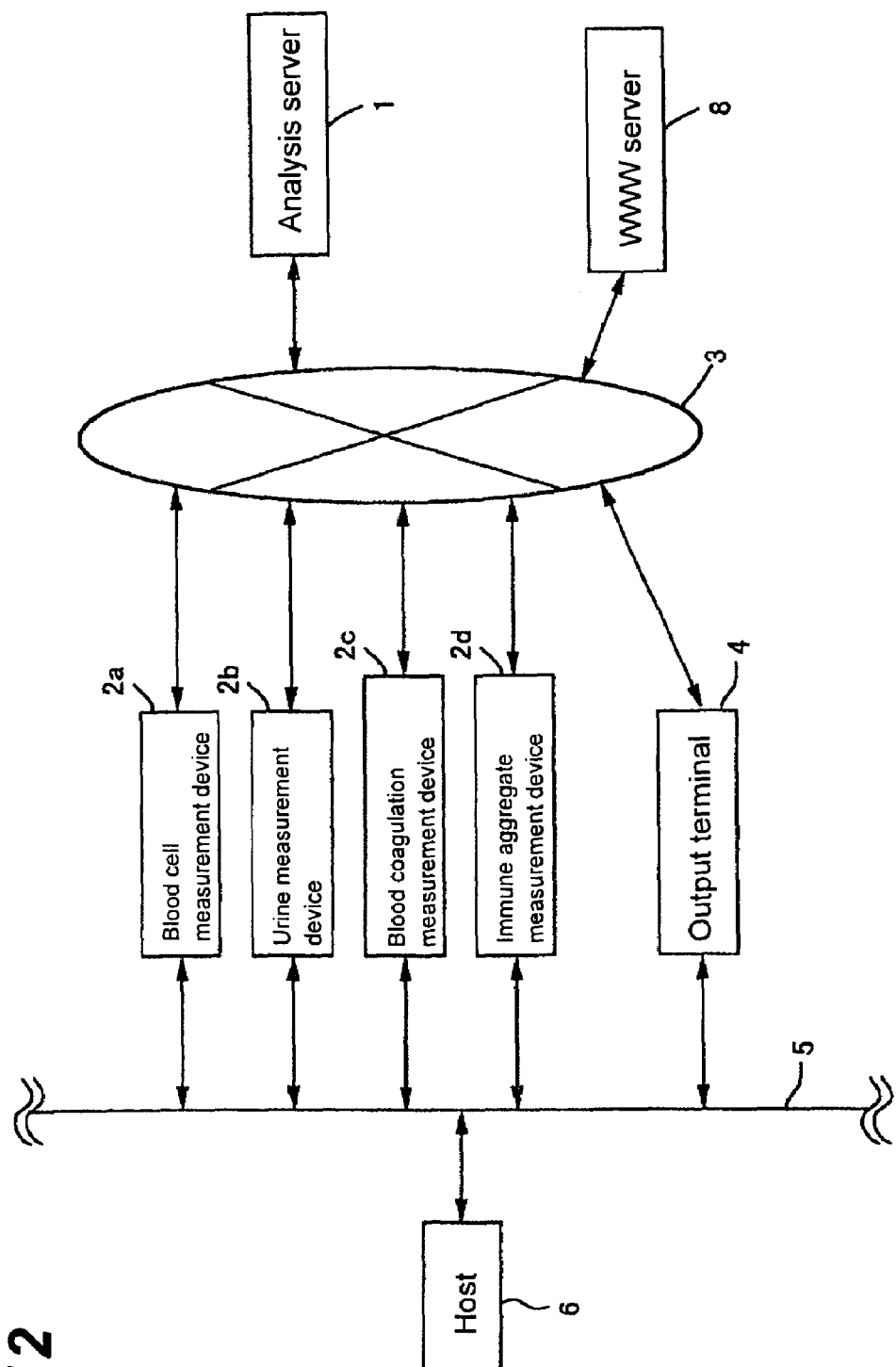
FIG. 12 is an example of the output of the analytical data of a sample.

FIG. 12 is an output example of the analytical data output by the output terminal 4. This figure indicates the coagulation curves for PT, APTT, Hbg, TT, and HPT, and analytical data.

Not only the coagulation time as analytical data, but also results of the calculated items obtained by analyzing the measurement data, the error messages obtained by monitoring and flagging messages are displayed in the analytical data as supplemental information.

Figure 13:
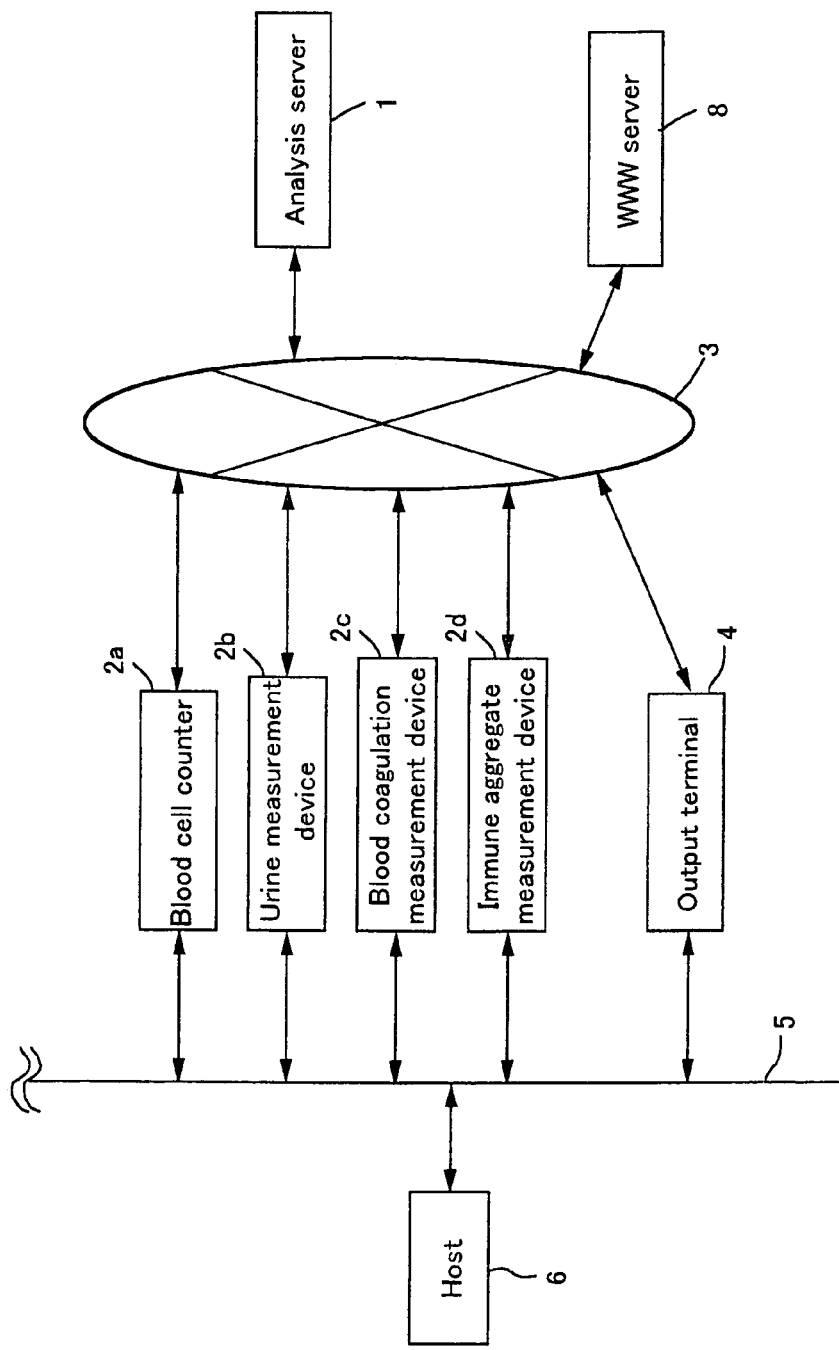
FIG. 13 is an overall configurational diagram of the analytical data production system of another embodiment.

Other Embodiments (A) An example of another configuration of an analytical Data Production System FIG. 13 is an example of the overall configuration of another embodiment of an analytical data production system. In the figure, the elements that have a function identical with the aforementioned first embodiment have the same reference numerals. In this example, WWW server 8 is provided as a substitute for patient DB 7. Patient data for each user are stored in this WWW server 8. Users can refer to analytical data on patient examinations on a web page by using a browser and accessing WWW server 8.

Further, not only analytical data on examinations can be stored on WWW server 8, but also other data that relate to patients. For example, WWW server 8 produces a web page for each patient, and publishes examination results, as well as illness history, medication history, accounting data and the like on each patient's web page. Access to the web pages is controlled by password, user ID, or other types of authentication information.

(B) The billing system is not limited to the system discussed above. A variety of billing systems can be applied according to such things like commercial need, an individual user's needs, and the like.

(C) Other examples of measurement data and analytical data

In the aforementioned embodiment, an example of the measurement device 2 was a device that measures blood coagulation time. However, the measurement device 2 is not particularly limited thereto if it is capable of measuring data for in vitro test and in vivo test. For example, measurement data and their analysis will be explained in a situation in which the measurement device 2 is a modified PAMIA-50 immune aggregate measuring device. A modification of a PAMIA-50 to a immune aggregate measuring device that can be used in the present invention can be achieved in the same way that the aforementioned CA-1500 was modified to a blood coagulation measurement device that can be used in the present invention.

Figure 14:
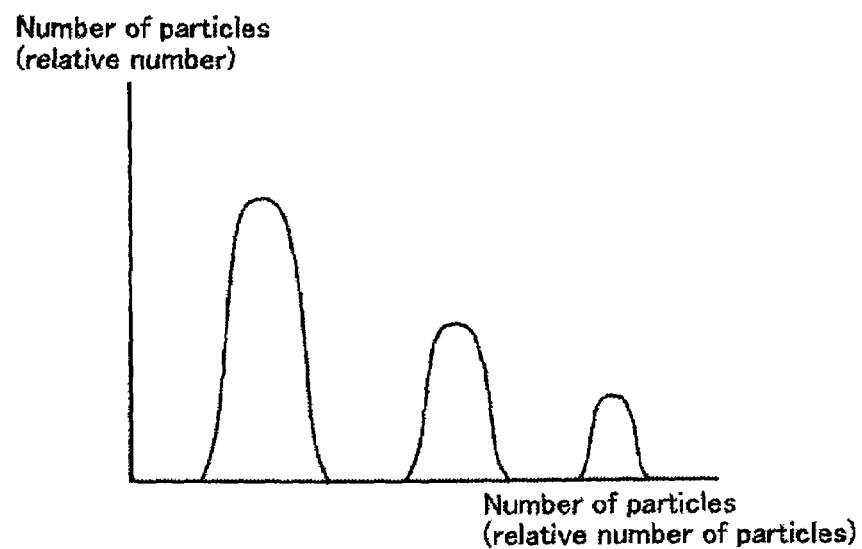
FIG. 14 is a graph that is employed by an example (an analysis of the degree of aggregation) of the analysis process.
Figure 15:
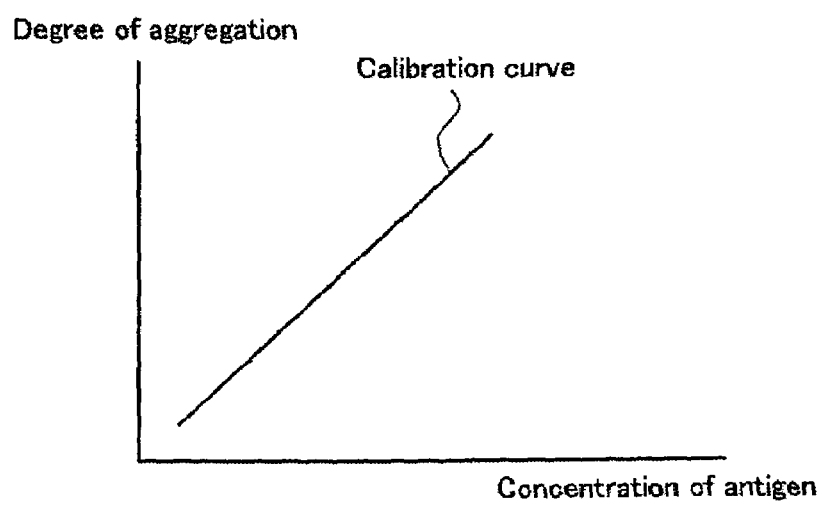
FIG. 15 is an explanatory diagram showing an example of a calibration curve.

The immune aggregate measuring device is a device that measures the concentration of antigens by affixing a reagent to a collected sample, producing an antigen-antibody reaction, and measuring the aggregation. Measurement data that pair up the measurement time with the intensity of the scattered light can be obtained from this device. The analysis of measurement data takes place as follows.

a: The particle size distribution graph illustrated in FIG. 14 is obtained from the obtained measurement data, and the degree of aggregation is obtained from the particle size distribution graph (=aggregate particle size/total number of particles). A method of producing a particle size distribution graph is disclosed, for example, in Japanese Patent Application Laid-Open Publication No. H3-279842.

b: The degree of aggregation obtained is adapted to a graph produced previously with latex particles that have a known concentration, thereby obtaining the antigen concentration, i.e., analytical data. FIG. 15 is a description showing an example of a calibration curve. In addition, in the event that the reagent lot is modified, it will be necessary to reproduce the calibration graph as well.

Conventionally, because the analysis unit 12 was inside the test device, the user had to produce the calibration graph as well. However, by using the system of the present invention, the service provider can produce the calibration graph, which reduces the burden on the user.

<Supplement 1>

As discussed previously, it is possible for the service provider to completely produce the calibration curve. However, the calibration curve may be produced by the following procedures in order to minimize the discrepancies in each measurement device.

a: Conducting calibrator measurements by the measurement device 2.

b: Transmitting calibrator measurement data and calibrator information (calibrator particle size and lot number) from the measurement device 2 to the analysis server 1.

c: The analysis server 1 produces the calibration curve shown in FIG. 15 from the calibrator measurement data received and calibrator information (calibrator particle size and lot number).

<Supplement 2>

It is necessary to produce a calibration curve for each reagent lot. However, there may be also cases in which the reagent that the user uses and the calibration curve that the analysis server 1 possesses do not match. In order to protect against this, the measurement data are transmitted to the analysis server 1 from the measurement device 2 together with the reagent lot number. The analysis server 1 determines whether or not the reagent lot number and the calibration curve match. The analysis server 1 continues analysis as is if both match, and if both do not match, requires output terminal 4 to display a message such as "Please measure the calibrator" or the like.

(D) Other aspects of output terminal 4.

Figure 16:
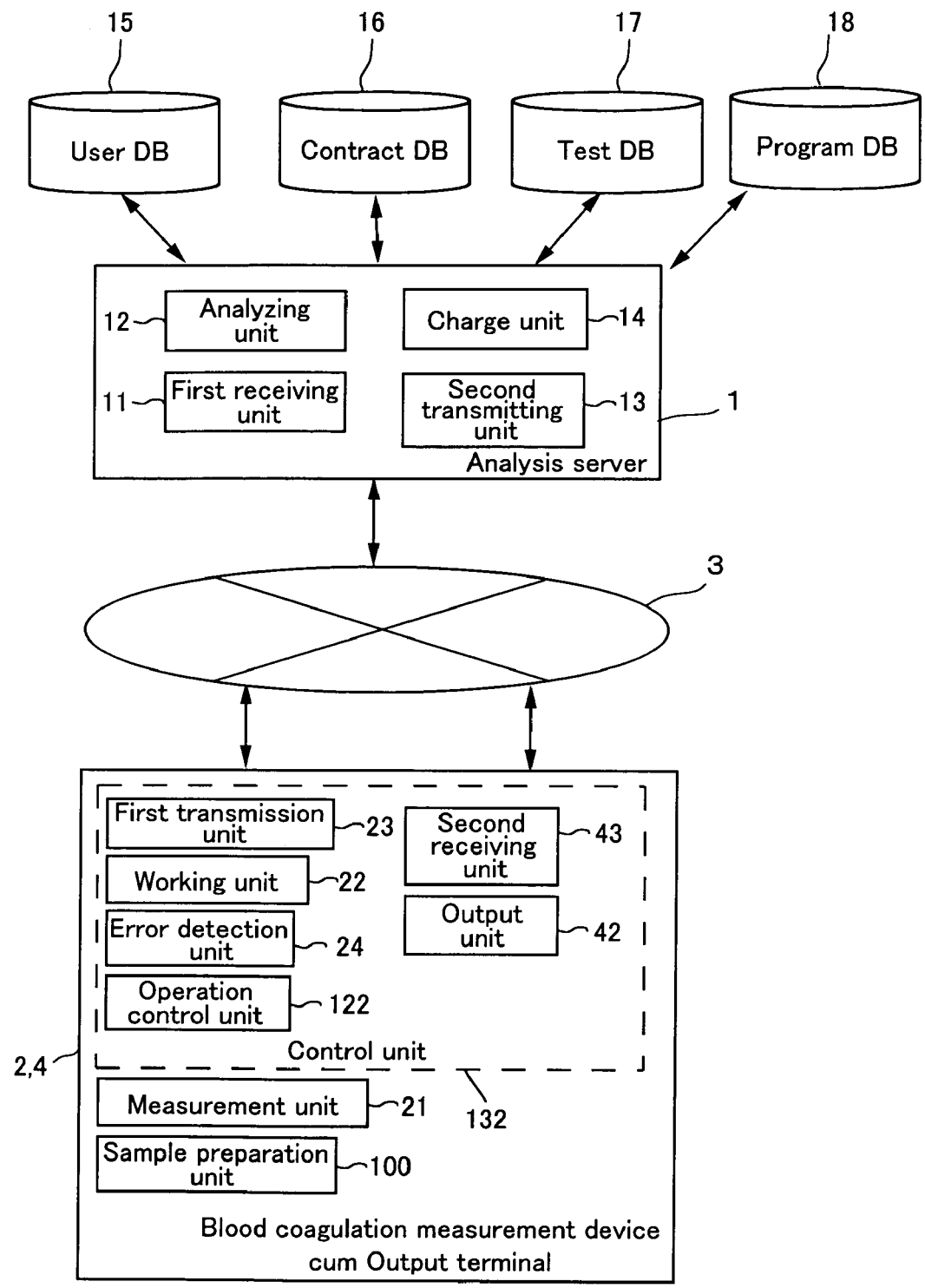
FIG. 16 is an explanatory diagram showing another aspect of the output terminal (an example in which the output terminal and measurement device was effectuated in one computer)

FIG. 16 shows a configuration in which the output terminal 4 and the measurement device 2 are effectuated in one computer terminal. In the figure, the elements that have the same function of those in the first embodiment are referred to with the same reference numerals.

Figure 17:
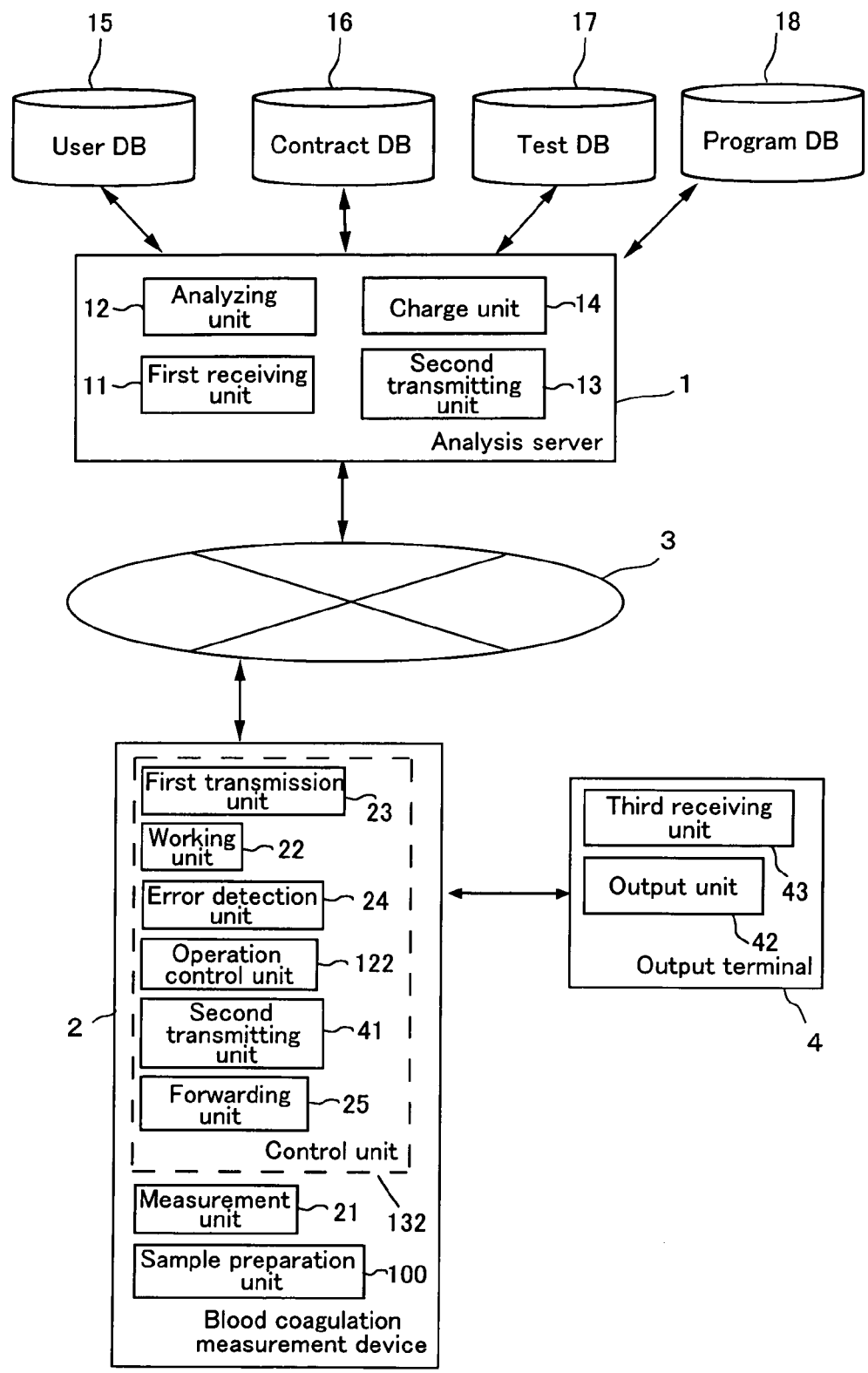
FIG. 17 is an explanatory diagram showing another aspect of the output terminal (an example of a configuration in which analytical data is obtained from the measurement device)

In addition, FIG. 17 shows the configuration in which the measurement device 2 and the output terminal 4 are connected by a communication interface such as an RS232C and the like. In the figure, the elements that have the same function of those in the first embodiment are referred to with the same reference numerals. The measurement device 2 further includes a second receiving unit 41 that receives working data from the analysis server 1, and a forwarding unit 25 that forwards working data to the output terminal 4. The output terminal 4 is further provided with a third receiving portion 43 that receives forwarded working data.

In addition, the measurement device 2 and the output terminal 4 can be connected by a network.

(E) The recording medium used to record the programs that carry out the process of the present invention discussed previously and the programs themselves are included in the present invention. Here, for the recording medium, a floppy disk, hard disk drive, semiconductor memory, CD-ROM, DVD, magneto-optical disk (MO), etc. that a computer is capable of reading from and writing to can be cited.

According to the present invention, a user can quickly respond to changes in the medical environment. In addition, the service provider can provide a detailed level of user support. Moreover, it is not necessary for the user to make a large initial investment.

While only selected embodiments have been chosen to illustrate the present invention, to those skilled in the art it will be apparent from this disclosure that various changes and modifications can be made herein without departing from the scope of the invention as defined in the appended claims. Furthermore, the foregoing description of the embodiments according to the present invention is provided for illustration only, and not for the purpose of limiting the invention as defined by the appended claims and their equivalents.

What is claimed is:

1. A measurement device to be connected via a network to an analysis device that processes measurement data and converts said measurement data into an analytical result, comprising:

measurement means for measuring a subject and/or a sample obtained from said subject and obtaining measurement data, first transmission means for transmitting said measurement data to said analysis device via said network, said analysis device converting said measurement data into said analytical result, said analytical result including said subject's in vivo and/or in vitro test result, which is a result of analysis of said measurement data, and error detection means for detecting an error during the measurement by said measurement means, wherein said measurement means stops the obtainment of measurement data if said error detection means detects an error, and said network is selected from the group consisting of an internet, a public telephone network, a mobile communication network, and an ISDN.

2. The measurement device according to claim 1, further comprising
output means for outputting said analytical result received from said analysis device.

3. The measurement device according to claim 2, wherein said output means comprises a computer.

4. The measurement device according to claim 1, wherein said first transmission means associates a communication address of said measurement device with said measurement data and transmits said measurement data.

5. The measurement device according to claim 1, wherein said first transmission means associates identification information of said subject and test items with said measurement data and transmits said measurement data.

6. The measurement device according to claim 1, wherein said first transmission means associates device identification information that indicates the identity of said measurement device with said measurement data and transmits said measurement data.

7. The measurement device according to claim 1, further comprising:
output means for outputting said analytical result,
receiving means for receiving from said analysis device said analytical result obtained by processing said measurement data, and
second transmission means for transmitting said analytical result received by said receiving means to said output means.

8. A method of producing an analytical result, comprising:
a measurement step of obtaining measurement data by a measurement device for measuring a subject and/or a sample obtained from said subject,
a first transmission step of transmitting said measurement data from said measurement device to an analysis device via a network,
a first receiving step of receiving said measurement data by said analysis device,
a processing step of processing said measurement data by said analysis device to convert said measurement data into an analytical result, said analytical result including said subject's in vivo and/or in vitro test result, which is a result of analysis of said measurement data,
a second transmission step of transmitting said analytical result from said analysis device, via said network, to said measurement device,
a second receiving step of receiving said analytical result by said measurement device,
an error detection step of determining whether there is an error during said measurement step, and
a stopping step of stopping said measurement step by said measurement device if an error is detected during said error detection step.

9. The method of producing an analytical result according to claim 8, wherein
said first transmission step includes a step of associating a communication address of said measurement device with said measurement data.

10. The method of producing an analytical result according to claim 8, further comprising:
an outputting step of outputting said analytical result by said measurement device.

11. The method of producing an analytical result according to claim 8, wherein
said network is selected from the group consisting of an internet, a public telephone network, a mobile communication network, and an ISDN.

12. An analytical result producing device, comprising:
receiving means for receiving measurement data via a network from a measurement device that measures a subject and/or a sample obtained from said subject and obtains said measurement data,
processing means for processing said measurement data, and converting said measurement data into an analytical result, said analytical result including said subject's in vivo and/or in vitro test result, which is a result of analysis of said measurement data, and
transmission means for transmitting, via said network, said analytical result to said measurement device,
wherein
said receiving means further receives device identification information that identifies a class of said measurement device and said measurement data associated therewith, and
said processing means includes:
storage means for storing analysis programs for processing said measurement data for each class of said measurement device,
determination means for determining said class of said measurement device based upon said device identification information, and
selection means for selecting an analysis program corresponding to said class of said measurement device from amongst said stored analysis programs, and for applying the selected analysis program to the processing of said measurement data.

13. The analytical result producing device according to claim 12, wherein
said receiving means receives a communication address of said measurement device and associates said communication address with said measurement data.

14. The analytical result producing device according to claim 12, wherein
said receiving means further receives identification information and test items for said subject that are associated with said measurement data, and
said transmission means transmits said identification information of said subject and said test items associated with said measurement data.

15. The analytical result producing device according to claim 12, further comprising:
results storage means for storing conditions on a contract relating to the processing of measurement data exchanged between a manager of the analytical result producing device and a manager of said measurement device, and usage results of said analytical result producing device that said manager of said measurement device used, and
determination means for determining items billed to said manager of said measurement device based on said contract conditions and said usage results.

16. An analytical result producing device, comprising:
receiving means for receiving measurement data via a network from a measurement device that measures a subject and/or a sample obtained from said subject and obtains said measurement data,
processing means for processing said measurement data, and converting said measurement data into an analytical result, said analytical result including said subject's in vivo and/or in vitro test result, which is a result of analysis of said measurement data, and
transmission means for transmitting, via said network, said analytical result to an output device that outputs said analytical result, wherein
said receiving means further receives device identification information that identifies a class of said measurement device and said measurement data associated therewith, and said processing means includes:
storage means for storing analysis programs for processing said measurement data for each class of said measurement device,
determination means for determining said class of said measurement device based upon said device identification information, and
selection means for selecting an analysis program corresponding to said class of said measurement device from amongst said stored analysis programs, and for applying the selected analysis program to the processing of said measurement data.

17. The analytical result producing device according to claim 16, wherein
said receiving means receives a communication address of said measurement device and associates said communication address with said measurement data.

18. The analytical result producing device according to claim 16, wherein
said receiving means further receives identification information and test items for said subject that are associated with said measurement data, and
said transmission means transmits said identification information of said subject and said test items associated with said analytical result.

19. The analytical result producing device according to claim 16, further comprising:
results storage means for storing conditions on a contract relating to the processing of measurement data exchanged between a manager of the analytical result producing device and a manager of said measurement device, and usage results of said analytical result producing device that said manager of said measurement device used, and
determination means for determining items billed to said manager of said measurement device based on said contract conditions and said usage results.

20. A system of producing an analytical result, comprising:
a measurement device, and
an analysis device to be connected via a network to said measurement device,
wherein
said measurement device comprises
measurement means for measuring a subject and/or a sample obtained from said subject and obtaining measurement data,
first transmission means for transmitting, via said network, said measurement data to said analysis device, and
error detection means for detecting an error during the measurement by said measurement means,
said measurement means stops the obtainment of measurement data if said error detection means detects an error, and
said analysis device comprises
receiving means for receiving said measurement data from said measurement device via said network,
processing means for processing said measurement data, and converting said measurement data into an analytical result, said analytical result including said subject's in vivo and/or in vitro test result, which is a result of analysis of said measurement data, and
second transmission means for transmitting, via said network, said analytical result to said measurement device.

21. The system according to claim 20, wherein
said measurement device further comprises output means for outputting said analytical result.

22. The system according to claim 20, wherein
said network is selected from the group consisting of an internet, a public telephone network, a mobile communication network, and an ISDN.

23. The system according to claim 20, further comprising:
a web server for storing patient data.

24. A method of producing an analytical result, comprising:
a measurement step of obtaining measurement data by a measurement device for measuring a subject and/or a sample obtained from said subject,
a first transmission step of transmitting said measurement data from said measurement device to an analysis device via a network,
a first receiving step of receiving said measurement data by said analysis device,
a processing step of processing said measurement data by said analysis device to convert said measurement data into an analytical result, said analytical result including said subject's in vivo and/or in vitro test result, which is a result of analysis of said measurement data,
a second transmission step of transmitting said analytical result from said analysis device, via said network, to an output device that outputs said analytical result,
a second receiving step of receiving said analytical result by said output device,
an output step of outputting said analytical result by said output device,
an error detection step of determining whether there is an error during said measurement step, and
a stopping step of stopping said measurement step by said measurement device if an error is detected during said error detection step.

25. The method of producing an analytical result according to claim 24, wherein
said first transmission step includes a step of associating a communication address of said output device with said measurement data.

26. The method of producing an analytical result according to claim 24, wherein
said network is selected from the group consisting of an internet, a public telephone network, a mobile communication network, and an ISDN.

27. A system of producing an analytical result, comprising:
a measurement device,
an analysis device to be connected via a network to said measurement device, and
an output device to be connected via said network to said analysis device,
wherein said measurement device comprises
measurement means for measuring a subject and/or a sample obtained from said subject and obtaining measurement data,
first transmission means for transmitting said measurement data to said analysis device via said network, and error detection means for detecting an error during the measurement by said measurement means, said measurement means stops the obtainment of measurement data if said error detection means detects an error, said analysis device comprises
- first receiving means for receiving said measurement data from said measurement device via said network,
- processing means for processing said measurement data, and converting said measurement data into an analytical result, said analytical result including said subject's in vivo and/or in vitro test result, which is a result of analysis of said measurement data, and
- second transmission means for transmitting, via said network, said analytical result to said output device, and said output device comprises
- second receiving means for receiving said analytical result from said analysis device via said network, and
- output means for outputting said analytical result.

28. The system according to claim 27, wherein said network is selected from the group consisting of an internet, a public telephone network, a mobile communication network, and an ISDN.

29. The system according to claim 27, further comprising: a web server for storing patient data.

30. An output device to be connected to an analysis device via a network, comprising:
- receiving means for receiving an analytical result, via said network, from said analysis device that processes measurement data and converts said measurement data into said analytical result, said analytical result including a subject's in vivo and/or in vitro test result, which is a result of analysis of said measurement data, and
- output means for outputting said analytical result, wherein
- said analysis device is connected via said network to a measurement device that measures said subject and/or a sample obtained from said subject and obtains said measurement data, and
- said measurement device stops the obtainment of measurement if an error is detected during said measurement.

31. The output device according to claim 30, wherein said receiving means receives identification information and test items for said subject that are related to said analytical result, and said output device associates said subject's identification information and test items with said analytical result and outputs said analytical result.

32. A computer program product for analytical result production, comprising:
- receiving means for receiving measurement data via a network from a measurement device that measures a subject and/or a sample obtained from said subject and obtains said measurement data,
- processing means for processing said measurement data, and converting said measurement data into an analytical result, said analytical result including said subject's in vivo and/or in vitro test result, which is a result of analysis of said measurement data, and
- transmission means for transmitting, via said network, said analytical result to said measurement device, wherein
said receiving means further receives device identification information that identifies a class of said measurement device and said measurement data associated therewith, and said processing means includes:
- storage means for storing analysis programs for processing said measurement data for each class of said measurement device,
- determination means for determining said class of said measurement device based upon said device identification information, and
- selection means for selecting an analysis program corresponding to said class of said measurement device from amongst said stored analysis programs, and for applying the selected analysis program to the processing of said measurement data.

33. A computer program product for analytical result production, comprising:
- receiving means for receiving measurement data via a network from a measurement device that measures a subject and/or a sample obtained from said subject and obtains said measurement data,
- processing means for processing said measurement data, and converting said measurement data into an analytical result, said analytical result including said subject's in vivo and/or in vitro test result, which is a result of analysis of said measurement data, and
- transmission means for transmitting, via said network, said analytical result to an output device that outputs said analytical result, wherein
said receiving means further receives device identification information that identifies a class of said measurement device and said measurement data associated therewith, and said processing means includes:
- storage means for storing analysis programs for processing said measurement data for each class of said measurement device,
- determination means for determining said class of said measurement device based upon said device identification information, and
- selection means for selecting an analysis program corresponding to said class of said measurement device from amongst said stored analysis programs, and for applying the selected analysis program to the processing of said measurement data.

34. A computer program product comprising:
- measurement means for measuring a subject and/or a sample obtained from said subject and obtaining measurement data,
- transmission means for transmitting via a network said measurement data to an analysis device that processes said measurement data and converts said measurement data into an analytical result, said analytical result including said subject's in vivo and/or in vitro test result, which is a result of analysis of said measurement data, and
- error detection means for detecting an error during the measurement by said measurement means, wherein
said measurement means stops the obtainment of measurement data if said error detection means detects an error, and said network is selected from the group consisting of an internet, a public telephone network, a mobile communication network, and an ISDN.

35. An output device to be connected to a measurement device, comprising:

receiving means for receiving an analytical result from said measurement device, said analytical result being transmitted from an analysis device to said measurement device via a network, said measurement device measuring a subject and/or a sample obtained from said subject and obtaining measurement data, said measurement device stopping the obtainment of measurement data when an error is detected during the measurement of said subject and/or the sample obtained from said subject, said analysis device processing said measurement data and converting said measurement data into said analytical result, said analytical result including said subject's in vivo and/or in vitro test result, which is a result of analysis of said measurement data, and said measurement device being connected to said analysis device via said network, and output means for outputting said analytical result.

36. A measurement device to be connected via a network to an analysis device that processes measurement data and converts said measurement data into an analytical result, comprising:

a measurement unit for measuring a subject and/or a sample obtained from said subject and obtaining said measurement data, a transmission unit for transmitting said measurement data to said analysis device via said network to convert said measurement data into said analytical result, said analytical result including said subject's in vivo and/or in vitro test result, which is a result of analysis of said measurement data, and an error detection unit for detecting an error during the measurement by said measurement unit, wherein said measurement unit stops the obtainment of measurement data if said error detection unit detects an error, and said network is selected from the group consisting of an internet, a public telephone network, a mobile communication network, and an ISDN.

* * * * *